(12) United States Patent
Browning

(10) Patent No.: US 9,918,817 B2
(45) Date of Patent: *Mar. 20, 2018

(54) METHOD OF POST-OPERATIVELY ADJUSTING A URETHRAL SUPPORT IN TREATING URINARY INCONTINENCE OF A WOMAN

(71) Applicant: Coloplast A/S, Humlebaek (DK)

(72) Inventor: James Browning, Glasgow (GB)

(73) Assignee: Coloplast A/S, Humlebaek (DK)

( * ) Notice: Subject to any disclaimer, the term of this patent is extended or adjusted under 35 U.S.C. 154(b) by 150 days.

This patent is subject to a terminal disclaimer.

(21) Appl. No.: 14/740,276

(22) Filed: Jun. 16, 2015

(65) Prior Publication Data

US 2015/0272714 A1  Oct. 1, 2015

Related U.S. Application Data

(63) Continuation of application No. 14/151,873, filed on Jan. 10, 2014, now Pat. No. 9,089,394, which is a
(Continued)

(51) Int. Cl.
*A61F 2/00* (2006.01)
*A61B 17/04* (2006.01)
*A61B 17/00* (2006.01)

(52) U.S. Cl.
CPC ........ *A61F 2/0045* (2013.01); *A61B 17/0401* (2013.01); *A61B 2017/00805* (2013.01);
(Continued)

(58) Field of Classification Search
CPC .... A61F 2/0004; A61F 2/0036; A61F 2/0045; A61F 2/005; A61F 2/0063
(Continued)

(56) References Cited

U.S. PATENT DOCUMENTS

| 1,450,101 A | 3/1923 | Mathewson |
| 2,097,018 A | 10/1937 | Chamberlin |

(Continued)

FOREIGN PATENT DOCUMENTS

| CA | 2592617 C | 2/2004 |
| DE | 2305815 A1 | 8/1974 |

(Continued)

OTHER PUBLICATIONS

Ridley, John H. Appraisal of the Goebell-Frangenheim-Stoeckel Sling Procedure. American Journal of Obstetrics and Gynecology, 95(5):714-721, 1966.
(Continued)

*Primary Examiner* — John Lacyk
(74) *Attorney, Agent, or Firm* — Coloplast Corp., Coloplast A/S; Nick Baumann

(57) ABSTRACT

A method of post-operatively adjusting a urethral support in treating urinary incontinence of a woman is disclosed. The method includes passing a support through an incision and locating the support under a urethra. The support is a porous mesh adapted to allow tissue in-growth. The method include adjusting the support by applying tension to one of a first member that is secured to a first end of the support or a second member that is secured to a second end of the support. The first member and the second member each has an end that exits the skin. The first and second members are adapted to prevent tissue in-growth into the first member and the second member.

16 Claims, 13 Drawing Sheets

Related U.S. Application Data continuation of application No. 13/402,978, filed on Feb. 23, 2012, now Pat. No. 8,668,635, which is a continuation-in-part of application No. 12/072,901, filed on Feb. 28, 2008, now Pat. No. 8,167,785.

(52) U.S. Cl.
CPC ............ A61B 2017/0409 (2013.01); A61B 2017/0412 (2013.01); A61B 2017/0414 (2013.01); A61B 2017/0417 (2013.01); A61B 2017/0427 (2013.01); A61B 2017/0435 (2013.01); A61B 2017/0464 (2013.01); A61F 2250/0004 (2013.01)

(58) Field of Classification Search
USPC .................. 600/29–32, 37; 128/DIG. 25
See application file for complete search history.

(56) References Cited

U.S. PATENT DOCUMENTS

| | | |
|---|---|---|
| 2,427,176 A | 9/1947 | Aldeen |
| 2,738,790 A | 3/1956 | Todt, Sr. et al. |
| 3,054,406 A | 9/1962 | Usher |
| 3,124,136 A | 3/1964 | Usher |
| 3,126,600 A | 3/1964 | De Marre |
| 3,182,662 A | 5/1965 | Shirodkar |
| 3,311,110 A | 3/1967 | Singerman et al. |
| 3,384,073 A | 5/1968 | Winkle, Jr. |
| 3,472,232 A | 10/1969 | Earl |
| 3,580,313 A | 5/1971 | McKnight |
| 3,763,860 A | 10/1973 | Clarke |
| 3,789,828 A | 2/1974 | Schulte |
| 3,858,783 A | 1/1975 | Kapitanov et al. |
| 3,888,975 A | 6/1975 | Ramwell |
| 3,911,911 A | 10/1975 | Scommegna |
| 3,913,179 A | 10/1975 | Rhee |
| 3,913,573 A | 10/1975 | Gutnick |
| 3,916,899 A | 11/1975 | Theeuwes et al. |
| 3,924,633 A | 12/1975 | Cook et al. |
| 3,993,058 A | 11/1976 | Hoff |
| 3,995,619 A | 12/1976 | Glatzer |
| 4,019,499 A | 4/1977 | Fitzgerald |
| 4,037,603 A | 7/1977 | Wendorff |
| 4,128,100 A | 12/1978 | Wendorff |
| 4,172,458 A | 10/1979 | Pereyra |
| 4,233,968 A | 11/1980 | Shaw, Jr. |
| 4,235,238 A | 11/1980 | Ogiu et al. |
| 4,246,660 A | 1/1981 | Wevers |
| 4,409,866 A | 10/1983 | McBride |
| 4,441,497 A | 4/1984 | Paudler |
| 4,444,933 A | 4/1984 | Columbus et al. |
| 4,452,245 A | 6/1984 | Usher |
| 4,509,516 A | 4/1985 | Richmond |
| 4,632,100 A | 12/1986 | Somers et al. |
| 4,633,873 A | 1/1987 | Dumican et al. |
| 4,646,731 A | 3/1987 | Brower |
| 4,655,221 A | 4/1987 | Devereux |
| 4,769,038 A | 9/1988 | Bendavid et al. |
| 4,775,380 A | 10/1988 | Seedhom et al. |
| 4,784,139 A | 11/1988 | Demos |
| 4,799,484 A | 1/1989 | Smith et al. |
| 4,857,041 A | 8/1989 | Annis et al. |
| 4,865,031 A | 9/1989 | O'Keeffe |
| 4,873,976 A | 10/1989 | Schreiber |
| 4,911,164 A | 3/1990 | Roth |
| 4,920,986 A | 5/1990 | Biswas |
| 4,938,760 A | 7/1990 | Burton et al. |
| 5,004,468 A | 4/1991 | Atkinson |
| 5,013,292 A | 5/1991 | Lemay |
| 5,053,043 A | 10/1991 | Gottesman et al. |
| 5,085,661 A | 2/1992 | Moss |
| 5,112,344 A | 5/1992 | Petros |
| 5,123,428 A | 6/1992 | Schwarz |
| 5,123,910 A | 6/1992 | McIntosh |
| 5,149,329 A | 9/1992 | Richardson |
| 5,188,636 A | 2/1993 | Fedotov |
| 5,207,694 A | 5/1993 | Broome |
| 5,209,756 A | 5/1993 | Seedhom et al. |
| 5,219,352 A | 6/1993 | Atkinson |
| 5,234,436 A | 8/1993 | Eaton et al. |
| 5,250,033 A | 10/1993 | Evans |
| 5,256,133 A | 10/1993 | Spitz |
| 5,259,835 A | 11/1993 | Clark et al. |
| 5,281,237 A | 1/1994 | Gimpelson |
| 5,306,279 A | 4/1994 | Atkinson |
| 5,328,077 A | 7/1994 | Lou |
| 5,336,239 A | 8/1994 | Gimpelson |
| 5,337,736 A | 8/1994 | Reddy |
| 5,342,376 A | 8/1994 | Ruff |
| 5,356,432 A | 10/1994 | Rutkow et al. |
| 5,362,294 A | 11/1994 | Seitzinger |
| 5,368,595 A | 11/1994 | Lewis |
| 5,383,904 A | 1/1995 | Totakura et al. |
| 5,386,836 A | 2/1995 | Biswas |
| 5,397,353 A | 3/1995 | Oliver et al. |
| 5,403,328 A | 4/1995 | Shallman |
| 5,413,598 A | 5/1995 | Moreland |
| 5,434,146 A | 7/1995 | Labrie et al. |
| 5,439,467 A | 8/1995 | Benderev et al. |
| 5,456,711 A | 10/1995 | Hudson |
| 5,473,796 A | 12/1995 | Fusillo |
| 5,474,543 A | 12/1995 | McKay |
| 5,486,197 A | 1/1996 | Le et al. |
| 5,507,754 A | 4/1996 | Green et al. |
| 5,507,796 A | 4/1996 | Hasson |
| 5,520,700 A | 5/1996 | Beyar et al. |
| 5,522,896 A | 6/1996 | Prescott |
| 5,544,664 A | 8/1996 | Benderev et al. |
| 5,549,619 A | 8/1996 | Peters et al. |
| 5,562,685 A | 10/1996 | Mollenauer et al. |
| 5,562,689 A | 10/1996 | Green et al. |
| 5,569,273 A | 10/1996 | Titone et al. |
| 5,571,139 A | 11/1996 | Jenkins, Jr. |
| 5,591,163 A | 1/1997 | Thompson |
| 5,611,515 A | 3/1997 | Benderev et al. |
| 5,628,756 A | 5/1997 | Barker, Jr. et al. |
| 5,633,286 A | 5/1997 | Chen |
| 5,645,568 A | 7/1997 | Chervitz et al. |
| 5,647,836 A | 7/1997 | Blake, III et al. |
| 5,655,270 A | 8/1997 | Boisvert |
| 5,669,935 A | 9/1997 | Rosenman et al. |
| 5,683,349 A | 11/1997 | Makower et al. |
| 5,689,860 A | 11/1997 | Matoba et al. |
| 5,693,072 A | 12/1997 | McIntosh |
| 5,695,525 A | 12/1997 | Mulhauser et al. |
| 5,697,931 A | 12/1997 | Thompson |
| 5,697,978 A | 12/1997 | Sgro |
| 5,720,766 A | 2/1998 | Zang et al. |
| 5,749,884 A | 5/1998 | Benderev et al. |
| 5,766,221 A | 6/1998 | Benderev et al. |
| 5,774,994 A | 7/1998 | Stein et al. |
| 5,807,403 A | 9/1998 | Beyar et al. |
| 5,816,258 A | 10/1998 | Jervis |
| 5,830,220 A | 11/1998 | Wan et al. |
| 5,836,314 A | 11/1998 | Benderev et al. |
| 5,836,315 A | 11/1998 | Benderev et al. |
| 5,840,011 A | 11/1998 | Landgrebe et al. |
| 5,842,478 A | 12/1998 | Benderev et al. |
| 5,851,229 A | 12/1998 | Lentz et al. |
| 5,860,425 A | 1/1999 | Benderev et al. |
| 5,899,909 A | 5/1999 | Claren et al. |
| 5,904,692 A | 5/1999 | Steckel et al. |
| 5,919,232 A | 7/1999 | Chaffringeon et al. |
| 5,922,026 A | 7/1999 | Chin |
| 5,934,283 A | 8/1999 | Willem et al. |
| 5,935,122 A | 8/1999 | Fourkas et al. |
| 5,944,732 A | 8/1999 | Raulerson et al. |
| 5,954,057 A | 9/1999 | Li |
| 5,971,967 A | 10/1999 | Willard |
| 5,972,000 A | 10/1999 | Beyar et al. |
| 5,988,171 A | 11/1999 | Sohn et al. |
| 5,990,378 A | 11/1999 | Ellis |
| 5,997,554 A | 12/1999 | Thompson |

(56) References Cited

U.S. PATENT DOCUMENTS

| | | |
|---|---|---|
| 6,005,191 A | 12/1999 | Tzeng et al. |
| 6,010,447 A | 1/2000 | Kardjian |
| 6,030,393 A | 2/2000 | Corlew |
| 6,031,148 A | 2/2000 | Hayes |
| 6,039,686 A | 3/2000 | Kovac |
| 6,042,534 A | 3/2000 | Gellman et al. |
| 6,042,536 A | 3/2000 | Tihon et al. |
| 6,042,583 A | 3/2000 | Thompson et al. |
| 6,048,306 A | 4/2000 | Spielberg |
| 6,048,351 A | 4/2000 | Gordon et al. |
| 6,050,937 A | 4/2000 | Benderev |
| 6,053,935 A | 4/2000 | Brenneman et al. |
| 6,056,688 A | 5/2000 | Benderev et al. |
| 6,063,094 A | 5/2000 | Rosenberg |
| 6,068,591 A | 5/2000 | Bruckner et al. |
| 6,071,290 A | 6/2000 | Compton |
| 6,074,341 A | 6/2000 | Anderson et al. |
| 6,077,216 A | 6/2000 | Benderev et al. |
| 6,090,116 A | 7/2000 | D'Aversa et al. |
| 6,106,545 A | 8/2000 | Egan |
| 6,110,101 A | 8/2000 | Tihon et al. |
| 6,117,067 A | 9/2000 | Gil-Vernet |
| 6,159,207 A | 12/2000 | Yoon |
| 6,162,962 A | 12/2000 | Hinsch et al. |
| 6,168,611 B1 | 1/2001 | Rizvi |
| 6,174,329 B1 | 1/2001 | Callol et al. |
| 6,190,401 B1 | 2/2001 | Green et al. |
| 6,197,036 B1 | 3/2001 | Tripp et al. |
| 6,200,330 B1 | 3/2001 | Benderev et al. |
| 6,221,005 B1 | 4/2001 | Bruckner et al. |
| 6,221,060 B1 | 4/2001 | Willard |
| 6,231,496 B1 | 5/2001 | Wilk et al. |
| 6,245,082 B1 | 6/2001 | Gellman et al. |
| 6,264,676 B1 | 7/2001 | Gellman et al. |
| 6,267,772 B1 | 7/2001 | Mulhauser et al. |
| 6,273,852 B1 | 8/2001 | Lehe et al. |
| 6,287,316 B1 | 9/2001 | Agarwal et al. |
| 6,292,700 B1 | 9/2001 | Morrison et al. |
| 6,302,840 B1 | 10/2001 | Benderev |
| 6,306,079 B1 | 10/2001 | Trabucco |
| 6,319,264 B1 | 11/2001 | Tormala et al. |
| 6,328,686 B1 | 12/2001 | Kovac |
| 6,328,744 B1 | 12/2001 | Harari et al. |
| 6,334,446 B1 | 1/2002 | Beyar |
| 6,336,731 B1 | 1/2002 | Chien |
| 6,352,553 B1 | 3/2002 | van der Burg et al. |
| 6,355,065 B1 | 3/2002 | Gabbay |
| 6,382,214 B1 | 5/2002 | Raz et al. |
| 6,387,041 B1 | 5/2002 | Harari et al. |
| 6,406,423 B1 | 6/2002 | Scetbon |
| 6,406,480 B1 | 6/2002 | Beyar et al. |
| 6,408,656 B1 | 6/2002 | Ory et al. |
| 6,418,930 B1 | 7/2002 | Fowler |
| 6,440,154 B2 | 8/2002 | Gellman et al. |
| 6,443,964 B1 | 9/2002 | Ory et al. |
| 6,461,332 B1 | 10/2002 | Mosel et al. |
| 6,475,139 B1 | 11/2002 | Miller |
| 6,478,727 B2 | 11/2002 | Scetbon |
| 6,478,791 B1 | 11/2002 | Carter et al. |
| 6,482,214 B1 | 11/2002 | Sidor, Jr. et al. |
| 6,491,703 B1 | 12/2002 | Ulmsten |
| 6,494,887 B1 | 12/2002 | Kaladelfos |
| 6,494,906 B1 | 12/2002 | Owens |
| 6,502,578 B2 | 1/2003 | Raz et al. |
| 6,506,190 B1 | 1/2003 | Walshe |
| 6,527,802 B1 | 3/2003 | Mayer |
| 6,530,943 B1 | 3/2003 | Hoepffner |
| 6,544,273 B1 | 4/2003 | Harari |
| 6,575,897 B1 | 6/2003 | Ory et al. |
| 6,575,998 B2 | 6/2003 | Beyar |
| 6,582,443 B2 | 6/2003 | Cabak et al. |
| 6,592,515 B2 | 7/2003 | Thierfelder et al. |
| 6,596,001 B2 | 7/2003 | Stormby et al. |
| 6,599,235 B2 | 7/2003 | Kovac |
| 6,599,318 B1 | 7/2003 | Gabbay |
| 6,599,323 B2 | 7/2003 | Melican et al. |
| 6,612,977 B2 | 9/2003 | Staskin et al. |
| 6,638,210 B2 | 10/2003 | Berger |
| 6,638,211 B2 | 10/2003 | Suslian et al. |
| 6,638,284 B1 | 10/2003 | Rousseau et al. |
| 6,641,524 B2 | 11/2003 | Kovac |
| 6,641,525 B2 | 11/2003 | Rocheleau et al. |
| 6,652,450 B2 | 11/2003 | Neisz et al. |
| 6,652,595 B1 | 11/2003 | Nicolo |
| 6,666,817 B2 | 12/2003 | Li |
| 6,669,706 B2 | 12/2003 | Schmitt et al. |
| 6,669,735 B1 | 12/2003 | Pelissier |
| 6,673,010 B2 | 1/2004 | Skiba et al. |
| 6,675,483 B2 | 1/2004 | Bond et al. |
| 6,679,896 B2 | 1/2004 | Gellman et al. |
| 6,689,047 B2 | 2/2004 | Gellman |
| 6,691,711 B2 | 2/2004 | Raz et al. |
| 6,695,855 B1 | 2/2004 | Gaston |
| 6,702,827 B1 | 3/2004 | Lund et al. |
| 6,737,371 B1 | 5/2004 | Planck et al. |
| 6,755,781 B2 | 6/2004 | Gellman |
| 6,764,474 B2 | 7/2004 | Nielsen et al. |
| 6,783,554 B2 | 8/2004 | Amara et al. |
| 6,786,861 B1 | 9/2004 | Pretorius |
| 6,830,052 B2 | 12/2004 | Carter et al. |
| 6,860,887 B1 | 3/2005 | Frankle |
| 6,878,756 B2 | 4/2005 | Cinelli et al. |
| 6,884,212 B2 | 4/2005 | Thierfelder et al. |
| 6,911,003 B2 | 6/2005 | Anderson et al. |
| 6,932,759 B2 | 8/2005 | Kammerer et al. |
| 6,936,052 B2 | 8/2005 | Gellman et al. |
| 6,953,428 B2 | 10/2005 | Gellman et al. |
| 6,960,160 B2 | 11/2005 | Browning |
| 7,025,063 B2 | 4/2006 | Snitkin et al. |
| 7,063,716 B2 | 6/2006 | Cunningham |
| 7,070,556 B2 | 7/2006 | Anderson et al. |
| 7,070,558 B2 | 7/2006 | Gellman et al. |
| 7,087,065 B2 | 8/2006 | Ulmsten et al. |
| 7,094,199 B2 | 8/2006 | Petros et al. |
| 7,112,171 B2 | 9/2006 | Rocheleau et al. |
| 7,112,210 B2 | 9/2006 | Ulmsten et al. |
| 7,131,943 B2 | 11/2006 | Kammerer |
| 7,131,944 B2 | 11/2006 | Jacquetin |
| 7,140,956 B1 | 11/2006 | Korovin et al. |
| 7,156,858 B2 | 1/2007 | Schuldt-Hempe et al. |
| 7,204,802 B2 | 4/2007 | De Leval |
| 7,229,404 B2 | 6/2007 | Bouffier |
| 7,288,063 B2 | 10/2007 | Petros et al. |
| 7,290,410 B2 | 11/2007 | Meneghin et al. |
| 7,297,102 B2 | 11/2007 | Smith et al. |
| 7,326,213 B2 | 2/2008 | Benderev et al. |
| 7,347,812 B2 | 3/2008 | Mellier |
| 7,371,245 B2 | 5/2008 | Evans et al. |
| 7,387,634 B2 | 6/2008 | Benderev |
| 7,410,460 B2 | 6/2008 | Benderev |
| 7,395,822 B1 | 7/2008 | Burton et al. |
| 7,404,819 B1 | 7/2008 | Darios et al. |
| 7,500,945 B2 | 3/2009 | Cox et al. |
| 7,517,313 B2 | 4/2009 | Thierfelder et al. |
| 7,527,633 B2 | 5/2009 | Rioux |
| 7,559,885 B2 | 7/2009 | Merade et al. |
| 7,594,921 B2 | 9/2009 | Browning |
| 7,601,118 B2 | 10/2009 | Smith et al. |
| 7,611,454 B2 | 11/2009 | De Leval |
| 7,614,258 B2 | 11/2009 | Cherok et al. |
| 7,621,864 B2 | 11/2009 | Suslian et al. |
| 7,628,156 B2 | 12/2009 | Astani et al. |
| 7,673,631 B2 | 3/2010 | Astani et al. |
| 7,686,760 B2 | 3/2010 | Anderson et al. |
| 7,691,050 B2 | 4/2010 | Gellman et al. |
| 7,713,188 B2 | 5/2010 | Bouffier |
| 7,722,528 B2 | 5/2010 | Arnal et al. |
| 7,740,576 B2 | 6/2010 | Hodroff et al. |
| 7,766,926 B2 | 8/2010 | Bosley, Jr. et al. |
| 7,789,821 B2 | 9/2010 | Browning |
| 7,794,385 B2 | 9/2010 | Rosenblatt |
| 7,815,662 B2 | 10/2010 | Spivey et al. |
| 7,927,342 B2 | 4/2011 | Rioux |
| 7,975,698 B2 | 7/2011 | Browning |

(56) References Cited

U.S. PATENT DOCUMENTS

| | | |
|---|---|---|
| 7,981,022 B2 | 7/2011 | Gellman et al. |
| 8,007,430 B2 | 8/2011 | Browning |
| 8,016,741 B2 | 9/2011 | Weiser et al. |
| 8,016,743 B2 | 9/2011 | Maroto |
| 8,047,983 B2 | 11/2011 | Browning |
| 8,092,366 B2 | 1/2012 | Evans |
| 8,097,007 B2 | 1/2012 | Evans et al. |
| 8,100,924 B2 | 1/2012 | Browning |
| 8,118,727 B2 | 2/2012 | Browning |
| 8,118,728 B2 | 2/2012 | Browning |
| 8,123,673 B2 | 2/2012 | Browning |
| 8,128,554 B2 | 3/2012 | Browning |
| 8,157,821 B2 | 4/2012 | Browning |
| 8,157,822 B2 | 4/2012 | Browning |
| 8,162,818 B2 | 4/2012 | Browning |
| 8,167,785 B2 * | 5/2012 | Browning .......... A61B 17/0401 600/30 |
| 8,182,412 B2 | 5/2012 | Browning |
| 8,182,413 B2 | 5/2012 | Browning |
| 8,182,545 B2 | 5/2012 | Cherok et al. |
| 8,215,310 B2 | 7/2012 | Browning |
| 8,273,011 B2 | 9/2012 | Browning |
| 8,449,450 B2 | 5/2013 | Browning |
| 8,454,492 B2 | 6/2013 | Browning |
| 8,469,875 B2 | 6/2013 | Suslian et al. |
| 8,469,877 B2 | 6/2013 | Browning |
| 8,512,223 B2 | 8/2013 | Browning |
| 8,574,148 B2 | 11/2013 | Browning et al. |
| 8,603,119 B2 | 12/2013 | Browning |
| 8,603,120 B2 | 12/2013 | Browning |
| 8,632,554 B2 | 1/2014 | Browning |
| 8,668,635 B2 | 3/2014 | Browning |
| 8,709,471 B2 | 4/2014 | Browning |
| 8,801,596 B2 | 8/2014 | Browning |
| 8,821,369 B2 | 9/2014 | Browning |
| 8,821,370 B2 | 9/2014 | Browning |
| 8,852,075 B2 | 10/2014 | Browning |
| 9,005,222 B2 | 4/2015 | Evans et al. |
| 2001/0000533 A1 | 4/2001 | Kovac |
| 2001/0018549 A1 | 8/2001 | Scetbon |
| 2001/0039423 A1 | 11/2001 | Skiba et al. |
| 2001/0049467 A1 | 12/2001 | Lehe et al. |
| 2001/0049538 A1 | 12/2001 | Trabucco |
| 2001/0051815 A1 | 12/2001 | Esplin |
| 2001/0053916 A1 | 12/2001 | Rioux |
| 2002/0005204 A1 | 1/2002 | Benderev et al. |
| 2002/0007222 A1 | 1/2002 | Desai |
| 2002/0022841 A1 | 2/2002 | Kovac |
| 2002/0028980 A1 | 3/2002 | Thierfelder et al. |
| 2002/0042658 A1 | 4/2002 | Tyagi |
| 2002/0049503 A1 | 4/2002 | Milbocker |
| 2002/0052612 A1 | 5/2002 | Schmitt et al. |
| 2002/0052653 A1 | 5/2002 | Durgin |
| 2002/0052654 A1 | 5/2002 | Darois et al. |
| 2002/0055748 A1 | 5/2002 | Gellman et al. |
| 2002/0058959 A1 | 5/2002 | Gellman |
| 2002/0068948 A1 | 6/2002 | Stormby et al. |
| 2002/0072694 A1 | 6/2002 | Snitkin et al. |
| 2002/0077526 A1 | 6/2002 | Kammerer et al. |
| 2002/0078964 A1 | 6/2002 | Kovac et al. |
| 2002/0082619 A1 | 6/2002 | Cabak et al. |
| 2002/0083949 A1 | 7/2002 | James |
| 2002/0091298 A1 | 7/2002 | Landgrebe |
| 2002/0091373 A1 | 7/2002 | Berger |
| 2002/0099258 A1 | 7/2002 | Staskin et al. |
| 2002/0099259 A1 | 7/2002 | Anderson et al. |
| 2002/0099260 A1 | 7/2002 | Suslian et al. |
| 2002/0103542 A1 | 8/2002 | Bilbo |
| 2002/0107430 A1 | 8/2002 | Neisz et al. |
| 2002/0107525 A1 | 8/2002 | Harari et al. |
| 2002/0115906 A1 | 8/2002 | Miller |
| 2002/0119177 A1 | 8/2002 | Bowman et al. |
| 2002/0128670 A1 | 9/2002 | Ulmsten et al. |
| 2002/0138025 A1 | 9/2002 | Gellman et al. |
| 2002/0147382 A1 | 10/2002 | Neisz et al. |
| 2002/0151762 A1 | 10/2002 | Rocheleau et al. |
| 2002/0151909 A1 | 10/2002 | Gellman et al. |
| 2002/0151910 A1 | 10/2002 | Gellman et al. |
| 2002/0156487 A1 | 10/2002 | Gellman et al. |
| 2002/0156488 A1 | 10/2002 | Gellman et al. |
| 2002/0161382 A1 | 10/2002 | Neisz et al. |
| 2002/0183588 A1 | 12/2002 | Fierro |
| 2002/0188169 A1 | 12/2002 | Kammerer et al. |
| 2002/0188301 A1 | 12/2002 | Dallara et al. |
| 2003/0004395 A1 | 1/2003 | Therin |
| 2003/0009181 A1 | 1/2003 | Gellman et al. |
| 2003/0023136 A1 | 1/2003 | Raz et al. |
| 2003/0023137 A1 | 1/2003 | Gellman |
| 2003/0023138 A1 | 1/2003 | Luscombe |
| 2003/0036676 A1 | 2/2003 | Scetbon |
| 2003/0050530 A1 | 3/2003 | Neisz et al. |
| 2003/0065246 A1 | 4/2003 | Inman et al. |
| 2003/0065402 A1 | 4/2003 | Anderson et al. |
| 2003/0069469 A1 | 4/2003 | Li |
| 2003/0078468 A1 | 4/2003 | Skiba et al. |
| 2003/0100954 A1 | 5/2003 | Schuldt-Hempe et al. |
| 2003/0130670 A1 | 7/2003 | Anderson et al. |
| 2003/0149440 A1 | 8/2003 | Kammerer et al. |
| 2003/0171644 A1 | 9/2003 | Anderson et al. |
| 2003/0176762 A1 | 9/2003 | Kammerer |
| 2003/0176875 A1 | 9/2003 | Anderson et al. |
| 2003/0191360 A1 | 10/2003 | Browning |
| 2003/0199732 A1 | 10/2003 | Suslian et al. |
| 2003/0212305 A1 | 11/2003 | Anderson et al. |
| 2003/0220538 A1 | 11/2003 | Jacquetin |
| 2004/0029478 A1 | 2/2004 | Planck et al. |
| 2004/0034373 A1 | 2/2004 | Schuldt-Hempe et al. |
| 2004/0039453 A1 | 2/2004 | Anderson et al. |
| 2004/0059356 A1 | 3/2004 | Gingras |
| 2004/0097974 A1 | 5/2004 | De Leval |
| 2004/0106847 A1 | 6/2004 | Benderev |
| 2004/0144395 A1 | 7/2004 | Evans et al. |
| 2004/0172048 A1 | 9/2004 | Browning |
| 2004/0231678 A1 | 11/2004 | Fierro |
| 2004/0243166 A1 | 12/2004 | Odermatt et al. |
| 2004/0249240 A1 | 12/2004 | Goldmann et al. |
| 2004/0249373 A1 | 12/2004 | Gronemeyer et al. |
| 2004/0249397 A1 | 12/2004 | Delorme et al. |
| 2004/0249473 A1 | 12/2004 | Delorme et al. |
| 2005/0000524 A1 | 1/2005 | Cancel et al. |
| 2005/0004576 A1 | 1/2005 | Benderev |
| 2005/0065486 A1 | 3/2005 | Fattman |
| 2005/0080317 A1 | 4/2005 | Merade |
| 2005/0107805 A1 | 5/2005 | Bouffier et al. |
| 2005/0131274 A1 | 6/2005 | Suslian et al. |
| 2005/0240076 A1 | 10/2005 | Neisz et al. |
| 2005/0277806 A1 | 12/2005 | Cristalli |
| 2005/0278037 A1 | 12/2005 | Delorme et al. |
| 2005/0283040 A1 | 12/2005 | Greenhalgh |
| 2006/0015069 A1 | 1/2006 | Evans et al. |
| 2006/0025649 A1 | 2/2006 | Smith et al. |
| 2006/0025783 A1 | 2/2006 | Smith et al. |
| 2006/0041185 A1 | 2/2006 | Browning |
| 2006/0058578 A1 | 3/2006 | Browning |
| 2006/0089524 A1 | 4/2006 | Chu |
| 2006/0089525 A1 | 4/2006 | Mamo et al. |
| 2006/0130848 A1 | 6/2006 | Carey |
| 2006/0205995 A1 | 9/2006 | Browning |
| 2006/0264698 A1 | 11/2006 | Kondonis et al. |
| 2007/0015953 A1 | 1/2007 | MacLean |
| 2007/0020311 A1 | 1/2007 | Browning |
| 2007/0032695 A1 | 2/2007 | Weiser |
| 2007/0032881 A1 | 2/2007 | Browning |
| 2007/0059199 A1 | 3/2007 | Labuschagne |
| 2007/0149555 A1 | 6/2007 | Kase et al. |
| 2007/0219606 A1 | 9/2007 | Moreci et al. |
| 2008/0021263 A1 | 1/2008 | Escude et al. |
| 2008/0161837 A1 | 7/2008 | Toso et al. |
| 2008/0161850 A1 | 7/2008 | Weisenburgh et al. |
| 2008/0167518 A1 | 7/2008 | Burton et al. |
| 2008/0196729 A1 | 8/2008 | Browning |
| 2008/0200751 A1 | 8/2008 | Browning |
| 2008/0281148 A1 | 11/2008 | Evans et al. |
| 2009/0123522 A1 | 5/2009 | Browning |

(56) References Cited

U.S. PATENT DOCUMENTS

| | | |
|---|---|---|
| 2009/0137862 A1 | 5/2009 | Evans et al. |
| 2009/0171377 A1 | 7/2009 | Intoccia et al. |
| 2009/0221868 A1 | 9/2009 | Evans |
| 2009/0287229 A1 | 11/2009 | Ogdahl |
| 2010/0022822 A1 | 1/2010 | Walshe |
| 2010/0056856 A1 | 3/2010 | Suslian et al. |
| 2010/0063351 A1 | 3/2010 | Witzmann et al. |
| 2010/0113869 A1 | 5/2010 | Goldman |
| 2010/0130814 A1 | 5/2010 | Dubernard |
| 2010/0198002 A1 | 8/2010 | O'Donnell |
| 2010/0222794 A1 | 9/2010 | Browning |
| 2010/0222974 A1 | 9/2010 | Nakamura et al. |
| 2010/0256442 A1 | 10/2010 | Ogdahl et al. |
| 2010/0274074 A1 | 10/2010 | Khamis et al. |
| 2010/0280308 A1 | 11/2010 | Browning |
| 2010/0298630 A1 | 11/2010 | Wignall |
| 2011/0021868 A1 | 1/2011 | Browning |
| 2011/0034759 A1 | 2/2011 | Ogdahl et al. |
| 2011/0105833 A1 | 5/2011 | Gozzi |
| 2011/0124954 A1 | 5/2011 | Ogdahl et al. |
| 2011/0124956 A1 | 5/2011 | Mujwid et al. |
| 2011/0201872 A1 | 8/2011 | Browning |
| 2011/0230705 A1 | 9/2011 | Borwning |
| 2011/0230708 A1 | 9/2011 | Browning |
| 2011/0230709 A1 | 9/2011 | Browning |
| 2011/0237676 A1 | 9/2011 | Browning |
| 2011/0237865 A1 | 9/2011 | Browning |
| 2011/0237866 A1 | 9/2011 | Browning |
| 2011/0237867 A1 | 9/2011 | Browning |
| 2011/0237868 A1 | 9/2011 | Browning |
| 2011/0237869 A1 | 9/2011 | Browning |
| 2011/0237870 A1 | 9/2011 | Browning |
| 2011/0237873 A1 | 9/2011 | Browning |
| 2011/0237874 A1 | 9/2011 | Browning |
| 2011/0237875 A1 | 9/2011 | Browning |
| 2011/0237877 A1 | 9/2011 | Browning |
| 2011/0237878 A1 | 9/2011 | Browning |
| 2011/0237879 A1 | 9/2011 | Browning |
| 2011/0238095 A1 | 9/2011 | Browning |
| 2011/0245594 A1 | 10/2011 | Browning |
| 2011/0282136 A1 | 11/2011 | Browning |
| 2011/0319705 A1 | 12/2011 | Browning |
| 2011/0319706 A1 | 12/2011 | Browning |
| 2012/0083649 A1 | 4/2012 | Suslian et al. |
| 2012/0083651 A1 | 4/2012 | Browning |
| 2012/0116154 A1 | 5/2012 | Evans et al. |
| 2012/0143000 A1 | 6/2012 | Browning |
| 2012/0149977 A1 | 6/2012 | Browning |
| 2012/0199133 A1 | 8/2012 | Browning |
| 2013/0281775 A1 | 10/2013 | Browning |
| 2013/0289340 A1 | 10/2013 | Browning |
| 2013/0289341 A1 | 10/2013 | Browning |
| 2014/0039244 A1 | 2/2014 | Browning |
| 2014/0039247 A1 | 2/2014 | Browning |
| 2014/0039248 A1 | 2/2014 | Browning |
| 2014/0051917 A1 | 2/2014 | Browning |
| 2014/0303429 A1 | 10/2014 | Evans et al. |
| 2014/0303430 A1 | 10/2014 | Evans et al. |

FOREIGN PATENT DOCUMENTS

| | | |
|---|---|---|
| DE | 4220283 A1 | 12/1993 |
| DE | 4304353 A1 | 4/1994 |
| DE | 10019604 C2 | 6/2002 |
| DE | 10211360 A1 | 10/2003 |
| EP | 0009072 A1 | 4/1980 |
| EP | 0024781 B1 | 8/1984 |
| EP | 0024780 B1 | 10/1984 |
| EP | 0248544 B1 | 4/1991 |
| EP | 0437481 B1 | 7/1991 |
| EP | 0139286 B1 | 8/1991 |
| EP | 0470308 A1 | 2/1992 |
| EP | 0556313 B1 | 8/1993 |
| EP | 0557964 A1 | 9/1993 |
| EP | 0632999 A1 | 1/1995 |
| EP | 0650703 A1 | 5/1995 |
| EP | 0706778 A1 | 4/1996 |
| EP | 0740925 B1 | 11/1996 |
| EP | 0745351 A2 | 12/1996 |
| EP | 0778749 B1 | 6/1997 |
| EP | 0854691 B1 | 7/1998 |
| EP | 0983033 B1 | 3/2000 |
| EP | 1093758 A1 | 4/2001 |
| EP | 0719527 B1 | 8/2001 |
| EP | 1151722 B1 | 11/2001 |
| EP | 1159921 A2 | 12/2001 |
| EP | 0643945 B1 | 3/2002 |
| EP | 1342454 B1 | 9/2003 |
| EP | 1545285 B1 | 6/2005 |
| EP | 1060714 B1 | 8/2006 |
| EP | 1274370 B1 | 9/2006 |
| EP | 1296614 B1 | 9/2006 |
| EP | 1353598 B1 | 10/2007 |
| EP | 0797962 B2 | 9/2009 |
| FR | 1274370 A | 10/1961 |
| FR | 2712177 A1 | 5/1995 |
| FR | 2732582 A1 | 10/1997 |
| FR | 2735015 A1 | 2/1998 |
| FR | 2811218 E | 11/2000 |
| FR | 2787990 A1 | 4/2001 |
| GB | 0378288 A | 8/1932 |
| GB | 2353220 A | 2/2001 |
| JP | 4452180 B2 | 11/2005 |
| RU | 2187251 C1 | 8/2002 |
| RU | 2196518 C2 | 1/2003 |
| SU | 1225547 A1 | 4/1986 |
| SU | 1342486 A1 | 10/1987 |
| SU | 1475607 A1 | 4/1989 |
| WO | WO1990003766 A1 | 4/1990 |
| WO | WO1991000714 A1 | 1/1991 |
| WO | WO1993017635 A1 | 9/1993 |
| WO | WO1993019678 A2 | 10/1993 |
| WO | WO1995033454 A1 | 12/1995 |
| WO | WO1996003091 A1 | 3/1996 |
| WO | WO1996006567 A1 | 3/1996 |
| WO | WO199706567 A1 | 2/1997 |
| WO | WO1997013465 A1 | 4/1997 |
| WO | WO1997022310 A2 | 6/1997 |
| WO | WO1997043982 A1 | 11/1997 |
| WO | WO1998019606 A1 | 5/1998 |
| WO | WO1998035606 A2 | 8/1998 |
| WO | WO1998035616 A1 | 8/1998 |
| WO | WO1998035632 A1 | 8/1998 |
| WO | WO1998057590 A1 | 12/1998 |
| WO | WO1999016381 A1 | 4/1999 |
| WO | WO1999052450 A1 | 10/1999 |
| WO | WO1999059477 A1 | 11/1999 |
| WO | WO2000007520 A1 | 2/2000 |
| WO | WO2000013601 A1 | 3/2000 |
| WO | WO2000015141 A1 | 3/2000 |
| WO | 2000018325 A1 | 4/2000 |
| WO | WO2000018319 A1 | 4/2000 |
| WO | 2000027304 A1 | 5/2000 |
| WO | WO2000038784 A1 | 7/2000 |
| WO | WO2000057812 A1 | 10/2000 |
| WO | 2000066030 A1 | 11/2000 |
| WO | WO2000064370 A1 | 11/2000 |
| WO | WO2000074594 A1 | 12/2000 |
| WO | WO2000074613 A1 | 12/2000 |
| WO | WO2000074633 A2 | 12/2000 |
| WO | WO2001006951 A1 | 2/2001 |
| WO | WO2001026581 A1 | 4/2001 |
| WO | WO2001039670 A1 | 6/2001 |
| WO | WO2001045589 A21 | 6/2001 |
| WO | 2001052750 A1 | 7/2001 |
| WO | WO2001052729 A2 | 7/2001 |
| WO | WO2001056499 A1 | 8/2001 |
| WO | WO2001080773 A1 | 11/2001 |
| WO | WO2002002031 A1 | 1/2002 |
| WO | 2002019946 A2 | 3/2002 |
| WO | 2002028315 A2 | 4/2002 |
| WO | WO2002026108 A2 | 4/2002 |
| WO | WO2002028312 A1 | 4/2002 |

(56) References Cited

FOREIGN PATENT DOCUMENTS

| | | |
|---|---|---|
| WO | WO2002030293 A1 | 4/2002 |
| WO | WO2002032284 A2 | 4/2002 |
| WO | WO2002032346 A1 | 4/2002 |
| WO | 2002039914 A1 | 5/2002 |
| WO | WO2002034124 A2 | 5/2002 |
| WO | WO2002039890 A2 | 5/2002 |
| WO | 2002058562 A1 | 8/2002 |
| WO | 2002058563 A1 | 8/2002 |
| WO | 2002058564 A2 | 8/2002 |
| WO | 2002058565 A2 | 8/2002 |
| WO | 2002062237 A1 | 8/2002 |
| WO | 2002065922 A1 | 8/2002 |
| WO | 2002065923 A1 | 8/2002 |
| WO | WO2002060371 A1 | 8/2002 |
| WO | WO2002065921 A1 | 8/2002 |
| WO | WO2002065944 A1 | 8/2002 |
| WO | 2002071931 A1 | 9/2002 |
| WO | WO2002069781 A2 | 9/2002 |
| WO | WO2002071953 A2 | 9/2002 |
| WO | WO2002078548 A1 | 10/2002 |
| WO | WO2002078552 A1 | 10/2002 |
| WO | WO2002078568 A1 | 10/2002 |
| WO | WO2002078571 A2 | 10/2002 |
| WO | 2002098322 A1 | 12/2002 |
| WO | WO2002098340 A1 | 12/2002 |
| WO | WO2003002027 A1 | 1/2003 |
| WO | 2003013369 A1 | 2/2003 |
| WO | WO2003013392 A1 | 2/2003 |
| WO | WO2003057074 A2 | 7/2003 |
| WO | WO2003068107 A1 | 8/2003 |
| WO | 2003075792 A1 | 9/2003 |
| WO | WO2003022260 B1 | 10/2003 |
| WO | WO2003086205 A2 | 10/2003 |
| WO | 2003096928 A1 | 11/2003 |
| WO | 2003096930 A1 | 11/2003 |
| WO | WO2003092546 A2 | 11/2003 |
| WO | WO2003094781 A1 | 11/2003 |
| WO | WO2004002370 A1 | 1/2004 |
| WO | WO2004002379 A1 | 1/2004 |
| WO | WO2004004600 A1 | 1/2004 |
| WO | 2004016196 A2 | 2/2004 |
| WO | WO2004012626 A1 | 2/2004 |
| WO | 2004019786 A1 | 3/2004 |
| WO | 2004012579 A2 | 5/2004 |
| WO | WO2004098461 A2 | 11/2004 |
| WO | WO2005018494 A1 | 3/2005 |
| WO | WO2006015031 A2 | 2/2006 |
| WO | WO2006015042 A1 | 2/2006 |
| WO | WO20051128420 A1 | 2/2006 |
| WO | WO2006136625 A1 | 12/2006 |
| WO | WO2007059199 A2 | 5/2007 |
| WO | WO2007149555 A2 | 12/2007 |
| WO | WO2008007086 A2 | 1/2008 |
| WO | WO2008018494 A1 | 2/2008 |

OTHER PUBLICATIONS

Schumpelick, V. et at., "Minimized polypropylene mesh for preperitoneal net plasty (PNP) of incisional hernias," Chirurg 70:422-430 (1999).
Shaw, W., "An Operation for the Treatment of Stress Incontinence," Br. Med. J. 1949:1070-1073.
Sheiner et al., "An unusual complication of obturator foramen arterial bypass," J. Cardiovasc. Surg., 1969, 10 (4):324-328.
Sirls and Leach, "Use of Fascia Lata for Pubovaginal Sling," Female Urology, 1996, Raz (ed.). W.B. Saunders Company, Chapter 32, pp. 376-381.
Sloan and Barwin, "Stress Incontinence of Urine: A Retrospective Study of the Complications and Late Results of Simple Suprapubic Suburethral Fascial Slings," J. Urol. 1973, 110:533-536.
Solyx™ SIS System, The Carrier Tip That Allows for Advanced Control, (Accessed: Feb. 28, 2011).
Sottner et al. "New Single-Incision Sling System MiniArc™ in treatment of the female stress urinary incontinence" Gynekologicko-porodnická klinika [Online] 2010, 75(2), pp. 101-104.
Spencer et al., "A Comparison of Endoscopic Suspension of the Vesical Neck with Suprapubic Vesicourethropexy for Treatment of Stress Urinary Incontinence," J. Urol., 1987, 137:411-415.
Spinosa, JP et al., Transobturator surgery for female stress incontinence: a comparative anatomical study of outside-in vs. inside-out techniques, BJU Intl., 100(5), pp. 1097-1102 (Nov. 2007).
Stamey, "Endoscopic Suspension of the Vesical Neck for Urinary Incontinence in Females," Annals of Surgery, 1980, 192(4):465-471.
Stanton, Stuart L. Suprapubic Approaches for Stress Incontinence in Women. The Journal of the American Geriatrics Society, 38(3):348-351, 1990.
Staskin et al., "The Gore-tex sling procedure for female sphincteric incontinence: indications, technique, and results," World J. Urol., 1997, 15:295-299.
Stothers et al., "Anterior Vaginal Wall Sling," Female Urology, 1996, Raz (ed.), W.B. Saunders Company, Chapter 35, pp. 395-398.
Surgimesh Sling Treatment of Incontinence http://www.aspide.com Mar. 4, 2011.
Ulmsten and Petros, "intravaginal Slingplasty (IVS): An Ambulatory Surgical Procedure for Treatment of Female Urinary Incontinence," Scand. J. Urol. Nephrol., 1995, 29:75-82.
Ulmsten et al., "A three-year follow up of tension free vaginal tape for surgical treatment of female stress urinary incontinence," Br. J. Obstet. Gynecol., 1999, 106:345-350.
Ulmsten et al., "An Ambulatory Surgical Procedure Under Local Anesthesia for Treatment of Female Urinary Incontinence," Int. Urogynecol. J., 1996, 7:81-86.
Ulmsten et al., "Different Biochemical Composition of Connective Tissue in Continent and Stress Incontinent Women," Acta Obstet. Gynecol. Scand., 1987, 66:455-457.
Ulmsten et al., "The unstable female urethra," Am. J. Obstet. Gynecol., 1982, 144:93-97.
Ulmsten, "Female Urinary Incontinence—A Symptom, Not a Urodynamic Disease. Some Theoretical and Practical Aspects on the Diagnosis and Treatment of Female Urinary Incontinence," Int. Urogynecol. J., 1995, 6:2-3.
Ulstem et al., "A Multicenter Study of Tension-Free Vaginal Tape (TVT) for Surgical Treatment of Stress Urinary Incontinence," Int. Urogynecol. J., 1998, 9:210-213.
U.S. Appl. No. 13/149,994, filed Jun. 1, 2011.
U.S. Appl. No. 10/106,086, filed Mar. 25, 2002.
U.S. Appl. No. 11/199,061, filed Aug. 8, 2005.
U.S. Appl. No. 60/279,794, fled Mar. 29, 2001.
U.S. Appl. No. 60/302,929, filed Jul. 3, 2001.
U.S. Appl. No. 60/307,836, filed Jul. 25, 2001.
U.S. Appl. No. 60/322,309, filed Sep. 14, 2001.
U.S. Appl. No. 60/362,606, filed Mar. 7, 2002.
U.S. Appl. No. 60/380,797, filed May 14, 2002.
U.S. Appl. No. 60/393,969, filed Jul. 5, 2002.
U.S. Appl. No. 60/402,007, filed Aug. 8, 2002.
U.S. Appl. No. 60/414,865, filed Sep. 30, 2002.
Webster and Kreder, "Voiding Dysfunction Following Cystourethropexy: Its Evaluation and Management," J. Urol., 1990, 144:670-673.
Weidemann, Small Intestinal Submucosa for Pubourethral Sling Suspension for the Treatment of Stress Incontinence: First Histopathologicai Results in Humans, Jul. 2004.
Winter, "Peripubic Urethropexy for Urinary Stress Incontinence in Women," Urology, 1982, 20(4):408-411.
Woodside and Borden, "Suprapubic Endoscopic Vesical Neck Suspension for the Management of Urinary Incontinence in Myelodysplastic Girls," J. Urol., 1986, 135:97-99.
Written Opinion for PCT/GB2009/050174, dated Jun. 24, 2009.
Written Opionion issued in PCT/GB2007/002589, dated Jan. 22, 2008, 5 pages.
Zacharin and Hamilton, "Pulsion Enterocele: Long-Term Results of an Abdominoperineal Technique," Obstet. Gynecol., 1980, 55(2):141-148.

(56) References Cited

OTHER PUBLICATIONS

Zacharin, "The suspensory mechanism of the female urethra," J. Anat., 1963, 97(3):423-427.
Moore et al. "Single-Center Retrospective Study of the Technique, Safety, and 12 Month Efficacy or the MiniArc™ Single Incision Sling: A New Minimally Invasive Procedure for Treatment of Female SUI" [Online] 2009, 18, pp. 175-181.
Morgan et al., "The Marlex sling operation for the treatment of recurrent stress urinary incontinence: A 16-year review," Am. J. Obstet. Gynecol., 1985, 151:224-226.
Morgan; "A sling operation, using Marlex polypropylene mesh, for treatment of recurrent stress incontinence," Am. J. Obstet. Gynecol., 1970, 106(3):369-376.
Narik and Paimrich, "A simplified sling operation suitable for routine use," Am. J. Obstet. Gynecol., 1962, 84:400-405.
Nichols, "The Mersilene Mesh Gauze-Hammock for Severe Urinary Stress Incontinence," Obstet. Gynecol., 1973, 41 (1):88-93.
Nicita, Giulio, (1998), "A New Operation for Genitourinary Prolapse," The Journal of Urology, 160:741-745.
Nickel et al., "Evaluation of a Transpelvic Sling Procedure With and Without Colpolsuspension for Treatment of Female Dogs With Refractory Urethral Sphincter Mechanism Incompetence," Veterinary Surgery, 1998, 27:94-104.
Norris et al., "Use of Synthetic Material in Sling Surgery: A Minimally Invasive Approach," J. Endocrinology, 1996, 10 (3):227-230.
Novak, "Abdonomovaginal Techniques," Gynecological Surgical Technique, 1977, Piccin Editore, Padua, 5 pages.
O'Donnell, "Combined Raz Urethral Suspension and McGuire Pubovaginal Sling for Treatment of Complicated Stress Urinary Incontinence," J. Arkansas Medical Society, 1992, 88(8):389.
Parra and Shaker, "Experience with a Simplified Technique for the Treatment of Female Stress Urinary Incontinence," British Journal of Urology, 1990, 66:615-617.
Pelosi II and Pelosi III, "New transobturator sling reduces risk of injury," OBG Management, 2003, pp. 17-37.
Pelosi II and Pelosi. Pubic Bone Suburethral Stabilization Sling: Laparoscopic Assessment of a Transvaginal Operation for the Treatment of Stress Urinary Incontinence. Journal of Laparoendoscopic & Advanced Surgical Techniques: 9(1): 45-50, 1999.
Penson and Raz, "Why Anti-incontinence Surgery Succeeds or Fails," Female Urology, 1996, Raz (ed.), W.B. Saunders Company, Chapter 41, pp. 435-442.
Pereyra et al., "Pubourethral Supports in Perspective: Modified Pereyra Procedure for Urinary Incontinence," Obstet Gynecol., 1982, 59:643-648.
Petros and Konsky, "Anchoring the rnidurethra restores bladder-neck anatomy and continence," The Lancet, 1999, 354:997-998.
Petros and Ulmsten, "An analysis of rapid pad testing and the history for the diagnosis of stress incontinence," Acta Obstet. Gynecol, Scand., 1992, 71:529-536.
Petros and Ulmsten, "An Anatomical Basis for Success and Failure of Female incontinence Surgery," Scand. J. Urol. Nephrol., 1993, (Suppl. 153):55-60.
Petros and Ulmsten, "Bladder instability in Women: A Premature Activation of the Micturition Reflex," Neurourology and Urodynamics, 1993, 12:235-239.
Petros and Ulmsten, "Cough Transmission Ratio: An Indicator of Suburethral Vaginal Wall Tension Rather than Urethral Closure?" Acta Obstet. Gynecol. Scand., 1990, 69(Suppl. 153):37-38.
Petros and Ulmsten, "Cure of Stress Incontinence by Repair of External Anal Sphincter," Acta. Obstet. Gynecol Scand., 1990, 69(Suppl. 153):75.
Petros and Ulmsten, "Cure of Urge Incontinence by the Combined Intravaginal Sling and Tuck Operation," Acta Obstet, Gynecol. Scand., 1990, 69(Suppl. 153)61-62.
Petros and Ulmsten, "Further Development of the Intravaginal Slingplasty Procedure—IVS III—(with midline "tuck")," Scand. J. Urol. Nephrol., Suppl. 153 An Integral Theory and its Method for the Diagnosis and Management of Female Urinary Incontinence: 69-71 , 1993.
Petros and Ulmsten, "Non Stress Non Urge Female Urinary Incontinence—Diagnosis and Cure: A Preliminary Report," Acta Obstet. Gynecol. Scand., 1990, 69(Suppl. 153):69-70.
Petros and Ulmsten, "Part I: Theoretical, Morphological, Radiographical Correlations and Clinical Perspective," Scand. J. Urol. Nephrol., 1993, Suppl. 153:5-28.
Petros and Ulmsten, "Part II:The Biomechanics of Vaginal Tissue and supporting Ligaments with Special Relevance to the Pathogenesis of Female Urinary Incontinence," Scand. J. Urol. Nephrol., 1993, Suppl. 153:29-40.
Petros and Ulmsten, "Part III: Surgical Principles Deriving from the Theory," Scand. J. Urol. Nephrol., 1993, Suppl. 153:41-52.
Petros and Ulmsten, "Part IV: Surgical Applications of the Theory—Development of the Intravaginal Sling Plasty (IVS) Procedure," Scand. J. Urol. Nephrol., 1993, Suppl. 153:53-54.
Petros and Ulmsten, "Pinch Test for Diagnosis of Stress Urinary Incontinence," Acta Obstet. Gynecol. Scand., 1990, 69(Suppl. 153):33-35.
Petros and Ulmsten. An Integral Theory of Female Urinary Incontinence. Acta Obstet. Gynecol. Scand., 1990, 69 (Suppl.153):7-31.
Petros and Ulmsten. Pregnancy Effects on the Intravaginal Sling Operation. Acta Obstet. Gynecol. Scand., 69(Suppl. 153 An Integral Theory of Female Urinary Incontinence) :77-78, 1990.
Petros arid Ulmsten. The Combined Intravaginal Sling and Tuck Operation. An Ambulatory Procedure for Cure of Stress and Urge Incontinence. Acta Obstet. Gynecol. Scand., 69(Suppl. 153 An Integral Theory of Female Urinary Incontinence): 53-59, 1990.
Petros and Ulmsten. The Development of the Intravaginal Slingplasty Procedure: IVS II—(with bilateral "tucks"). Scand. J. Urol. Nephrol., Suppl. 153 An Integral Theory and its Method for the Diagnosis and Management of Female Urinary Incontinence: 61-67, 1993.
Petros and Ulmsten. The Free Graft Procedure for Cure of the Tethered Vagina Syndrome, Scand. J. Urol. Nephrol., Suppl. 153: 85-87, 1997.
Petros and Ulmsten. The Further Development of the intravaginal Slingplasty Procedure: IVS IV—(with "double-breasted" unattached vaginal flap repair and "free" vaginal tapes). Scand. J. Urol. Nephrol., Suppl. 153 An Integral Theory and its Method for the Diagnosis arid Management of Female Urinary Incontinence: 73-79, 1993.
Petros and Ulmsten. The Intravaginal Slingplasty Procedure: IVS VI—Further Development of the "Double-Breasted" Vaginal Flap Repair—Attached Flap. Scand. J. Urol. Nephrol., Suppl. 153 An Integral Theory and its Method for the Diagnosis and Management of Female Urinary Incontinence: 81-84, 1993.
Petros and Ulmsten. The Posterior Fornix Syndrome: A Multiple Symptom Complex of Pelvic Pain and Abnormal Urinary Symptoms Deriving from Laxity in the Posterior Fornix of Vagina. Scand. J. Urol. Nephrol., Suppl. 153 An Integral Theory and its Method for the Diagnosis and Management of Female Urinary Incontinence: 89-93, 1993.
Petros and Ulmsten. The Role of a Lax Posterior Vaginal Fornix in the Causation of Stress and Urgency Symptoms: A Preliminary Report. Acta Obstet. Gynecol. Scand., 69(Suppl. 153 An Integral Theory of Female Urinary Incontinence): 71-73, 1990.
Petros and Ulmsten. The Tethered Vagina Syndrome, Post Surgical Incontinence and I-Plasty Operation for Cure. Acta Obstet. Gynecol. Scand., 69(Suppl.153 An Integral Theory of Female Urinary Incontinence): 63-67, 1990.
Petros and Ulmsten. The Tuck Procedure: A Simplified Vaginal Repair for Treatment of Female Urinary Incontinence. Acta Obstet. Gynecol. Scand., 69(Suppl.153 An Integral Theory of Female Urinary Incontinence): 41-42, 1990.
Petros and Ulmsten. Urethral Pressure Increase on Effort Originates From Within the Urethra, and Continence From Musculovaginal Closure. Neurourology and Urodynarnics, 14:337-350, 1995.
Petros, Peter E., et al., The Autogenic Ligament Procedure: A Technique for Planned Formation of an Artificial Neo-Ligament.

(56) References Cited

OTHER PUBLICATIONS

Acta Obstet. Gynecol. Scand., 69(Suppl. 153 An Integral Theory of Female Urinary Incontinence):43-51, 1990.
Petros. Development of Generic Models for Ambulatory Vaginal Surgery—A Preliminary Report. Int. Urogynecol. J., 9:19-27, 1998.
Product Monograph for Aris Transobturator Tape for the Treatment of Female Stress Urinary Incontinence, 2004, 40 pages.
Rackley, Raymond R., et al. Tension-free Vaginal Tape and Percutaneous Vaginal Tape Sling Procedures. Techniques in Urology, 7(2):90-100, 2001.
Rackley, Raymond. Synthetic Slings: Five Steps for Successful Placement—Follow These Steps to Insert Transvaginal/Percutaneous Slings Using Vaginal Approach Alone. Urology Times, 28:46-49, 2000.
Random House Webster's Unabridged Dictionary, 2001.
Raz, Shlomo, et al. The Raz Bladder Neck Suspension: Results in 206 Patients. The Journal of Urology: Urological Neurology and Urodynamics, 148:845-850, 1992.
Raz, Shlomo. Modified Bladder Neck Suspension for Female Stress Incontinence. Urology, 17(1):82-85, 1981.
Richardson, David A., et al. Delayed Reaction to the Dacron Buttress Used in Urethropexy. The Journal of Reproductive Medicine, 29(9):689-692, 1984.
Hohenfellner and Petri, "Sling Procedures," Surgery of Female Incontinence, 2nd edition, SpringerVerlag, pp. 105-113, 1986.
Holschneider et al., "The Modified Pereyra Procedure in Recurrent Stress Urinary Incontinence: A 15-Year Review," Obstet. Gynecol., 1994, 83:573-578.
Horbach et al., "A Suburethral Sling Procedure with Polytetrafluoroethylene for the Treatment of Genuine Stress Incontinence in Patients with Low Urethral Closure Pressure," Obstet. Gynecol., 1988, 71:648-652.
Horbach, "Suburethral Sling Procedures," Urogynecology and Urodynamics—Theory and Practice, 1996, Williams & Wilkins, pp. 569-579.
Ingelman-Sundberg and Ulmsten, "Surgical Treatment of Female Urinary Stress Incontinence," Contr. Gynec. Obstet., 1983, 10:51-69.
International Preliminary Examination Report issued in PCT/GB01/04554, completed Nov. 22, 2002, 6 pages.
International Search Report and Written Opinion issued in PCT/GB2004/001390, dated Sep. 3, 2004, 12 pages.
International Search Report for PCT/GB2009/050174, dated Jun. 24, 2009.
International Search Report issued in PCT/GB01/04554, dated Jan. 29, 2002, 3 pages.
International Search Report issued in PCT/GB2007/002589, dated Jan. 22, 2008, 5 pages.
Jacquetin, Bernard, "2. Utilisation du "TVT" dans la chirurgie de l'incontinence urinaire feminine", J. Gynecol. Obstet. Biol. Reprod. 29: 242-47 (2000).
Jeffcoate, "The Results of the Aldridge Sling Operation for Stress Incontinence," The Journal of Obstetrics and Gynaecology of the British Empire, 1956, 63:36-39.
Jeter, "The Social Impact of Urinary Incontinence," Female Urology, Raz (ed.), W. B. Saunders Company, 1996, Chapter 7, pp. 80-86.
Just-Swing(R) Adjustable mine-sling, Textile Hi-Tec Online Brochure 2010, 4 pages.
Karram and Bhatia, "Patch Procedure: Modified Transvaginal Fascia Lata Sling for Recurrent or Severe Stress Urinary Incontinence," Obstet Gynecol., 1990, 75:461-463.
Kennelly et al. "Prospective Evaluation of a Single Incision Sling for Stress Urinary Incontinence" The Journal of Urology [Online] 2010, 184, pp. 604-609.
Kerdiles et al., "Bypass via the Obturator Foramen in Reconstructive Arterial Surgery of the Lower Extremities," Ann. Chir. Thorac. Cardio-Vasc., 1974, 13(4):335-341.

Kerr and Staskiri, "The Use of Artificial Material for Sling Surgery in the Treatment of Female Stress Urinary Incontinence," Female Urology, 1996, Raz (ed.), W.B. Saunders Company, Chapter 33, pp. 382-391.
Kersey, "The gauze hammock sling operation in the treatment of stress incontinence," Br. J. Obstet. Gynecol., 1983, 90:945-949.
Klinge et al., "Functional and Morphological Evaluation of a Low-Weight, Monofilament Polypropylene Mesh for Hernia Repair," Journal of Biomedical Material Research, Jan. 24, 2002, pp. 129-137.
Klinge, U. et al., "Influence of polyglactin-coating on functional and morphological parameters of polypropylene-mesh modifications for abnormal wall repair," Biomaterials 20 (1999), pp. 613-623.
Klinge, U. et al., "Modified Mesh for Hernia Repair that is Adapted to the Physiology of the Abdominal Wall," Eur J Surg 164:951-960 (1998).
Klinge, U. et al., "Pathophysiology of the abdominal wall," Der Chirurg, (1996),67: 229-233.
Klosterhalfen, B, et al., "Functional and morphological evaluation of different polypropylene-mesh modifications for abdominal wall repair," Biomaterials 19:2235-2246 (1998).
Klosterhalfen, B. et al., "Morphological correlation of the functional mechanics of the abdominal wall after mesh implantation," Langenbecks Arch Chir 382:87-94 (1997).
Klutke et al., "The Anatomy of Stress Incontinence: Magnetic Resonance Imaging of the Female Bladder Neck and Urethra," J. Urol., 1990, 143:563-566.
Klutke et al., "Transvaginal Bladder Neck Suspension to Cooper's Ligament: A Modified Pereyra Procedure," Obstet, Gynecol., 1996, 88:294-297.
Korda et al., "Experience with Silastic Slings for Female Urinary Incontinence," Aust. NZ J. Obstet. Gynaecol., 1989, 29:150-154.
Kovac and Cruikshank. Pubic bone suburethral stabilization sling: a long-term cure for SUI? Contemporary OB/GYN: Surgical Techniques, 43(2):52-76, 1998.
Kovac, R. S. Follow-Up of the Pubic Bone Suburethral Stabilization Sling for Recurrent Urinary incontinence (Kovac Procedure). Journal of Pelvic Surgery, 5(3): 156-160, 1999.
Kovac, R., et. al. Pubic Bone Suburethral Stablization Sling for Recurrent Urinary Incontinence. Obstetrics & Genecology: Instruments & Methods, 89(4): 624-627, Apr. 1997.
Lazarevski, M.B., Suburethral Duplication of the Vaginal Wall—An Original Operation for Urinary Stress Incontinence in Women, 6 Int'l Urogynecol. J. 73-79 (1995).
Leach et al., "Female Stress Urinary Incontinence Clinical Guidelines Panel Summary Report on Surgical Management of Female Stress Urinary Incontinence," J. Urol., 1997, 158:875-880.
Leach, "Bone Fixation Technique for Transvaginal Needle Suspension," Urology, 1988, 31(5):388-390.
Lichtenstein et al., "The Tension-Free Hernioplasty," Am. J. Surgery, 1989, 157:188-193.
Lipton, S. and Estrin, J., "A Biomechanical Study of the Aponeurotic Iguinal Hernia Repair," Journal of the American College of Surgeons, Jun. 1994, vol. 178, pp. 595-599.
Loughlin et al., "Review of an 8-Year Experience with Modifications of Endoscopic Suspension of the Bladder Neck for Female Stress Urinary Incontinence," J. Urol., 1990, 143:44-45.
Maher, Surgical Management of Anterior Vaginal Wall Prolapse: An Evidence Based Literature Review, 2006.
Mahoney and Whelan, "Use of Obturator Foramen in Iliofemoral Artery Grafting: Case Reports," Annals of Surgery, 1966, 163(2):215-220.
Marshall et al., "The Correction of Stress Incontinence by Simple Vesicourethral Suspension," J. Urol., 2002, 168:1326-1331.
McGuire and Gormley, "Abdominal Fascial Slings," Female Urology, 1996, Raz (ed.), W.B. Saunders Company, Chapter 31, pp. 369-375.
McGuire and Lytton, "Pubovaginal Sling Procedure for Stress Incontinence," J. Urol., 1978, 119:82-84.
McGuire et al., "Experience with Pubovaginal Slings for Urinary Incontinence at the University of Michigan," J. Urol., 1987, 138:525-526.

(56) References Cited

OTHER PUBLICATIONS

McGuire, "Abdominal Procedures for Stress Incontinence," Urologic Clinics of North America, 1985, 12(2):285-290.
McIndoe et al., "The Aldridge Sling Procedure in the Treatment of Urinary Stress Incontinence," Aust. NZ J. Obstet. Gynaecol., 1987, 27:238-239.
McKiel, Jr. et al., "Marshall-Marchetti Procedure: Modification," J. Urol., 1966, 96:737-739.
Miklos, Mini Sling Incontinence Treatment—Vagina Plastic Surgery, http://www.miklosandmoore.com/mini_sling.php, Feb. 28, 2011.
MiniArc Single-Incision Sling http://www.americanmedicalsystems.com Mar. 4, 2011.
Moir, "The Gauze-Hammock Operation," The Journal of Obstetrics and Gynaecology of the British Commonwealth, 1968, 75(1):1-9.
Monseur, J., Anatomie Chirurgicale: Les Ligaments Du Perinee Feminin, Sep. 4, 2008.
Abdel-fattah, Mohamed et al. Evaluation of transobturator tapes (E-TOT) study: randomised prospective single-blinded study comparing inside-out vs. outside-in transobturator tapes in management of urodynamic stress incontinence: Short term outcomes, European Journal of Obstetrics & Gynecology and Reproductive Biology (2009).
Accelerated Examination Search for Surgical Implant—Abutment System and Method, Mar. 31, 2011, 10 pages.
Accelerated Examination Search for Surgical Implant—Adjustable, Mar. 4, 2011, 10 pages.
Accelerated Examination Search for Surgical Implant—Fiber Entanglement, Mar. 4, 2011, 8 pages.
Accelerated Examination Search for Surgical Implant—Introducer, Mar. 31, 2011, 12 pages.
Adjustable Mini-Sling, Just-Swing SVS "Secured Vaginal Sling", Polypropylene, Mar. 2010.
Ajust Adjustable Single-Incision Sling, http://www.bardnordic.com, Mar. 1, 2011.
Ajust(TM) Adjustable Single-Incision Sling, retrieved from www.barcinordic.com/main/product.asp?sectionTypeId=2§ion, accessed Mar. 1, 2011, 1 page.
Aldridge, "Transplantation of Fascia for Relief of Urinary Stress Incontinence," Am. J. Obstet. Gynecol., 1942, 44:398-411.
American Heritage Dictionary, 2nd College Edition (1991).
Araki et al., "The Loop-Loosening Procedure for Urination Difficulties After Stamey Suspension of the Vesical Neck," J. Urol., 1990, 144:319-323.
Asmussen and Ulmsten, "Simultaneous Urethro-Cystometry with a New Technique," Scand. J. Urol. Nephrol., 1976, 10:7-11.
Beck and McCormick, "Treatment of Urinary Stress incontinence with Anterior Colporrhaphy," Obstetrics and Gynecology, 1982, 59(3):271-274.
Benderev, "A Modified Percutaneous Outpatient Bladder Neck Suspension System," J. Urol., 1994, 152:2316-2320.
Benderev, "Anchor Fixation and Other Modifications of Endoscopic Bladder Neck Suspension," Urology, 1992, 40 (5):409-418.
Bergman and Elia, "Three surgical procedures for genuine stress incontinence: Five-year follow-up of a prospective randomized study," Am. J. Obstet. Gynecol., 1995, 173:66-71.
BioArc SP Sling Kit, www.AmericanMedicalSystems.com, 2006.
BioArc(R) SP Sling Kit: 12 Step Procedure, American Medical Systems Inc. Online Brochure 2006, 2 pages.
Blaivas and Jacobs, "Pubovaginal Fascial Sling for the Treatment of Complicated Stress Urinary Incontinence," J. Urol., 1991. 145:1214-1218.
Blaivas and Salinas, "Type III Stress Urinary Incontinence: Importance of Proper Diagnosis and Treatment," American College of Surgeons Surgical Forum, 1984, 70.sup.th Annual Clinical Congress, San Francisco, CA, vol. XXXV, pp. 473-474.
Botros, Cystocele and Rectocele Repair: More Success Wth Mesh? Jun. 2006.
Bryans, "Marlex gauze hammock sling operation with Cooper's ligament attachment in the management of recurrent urinary stress incontinence," Am. J. Obstet. Gynecol., 1979, 133(3):292-294.
Burch, "Urethrovaginal fixation to Cooper's ligament for correction of stress incontinence, cystocele, and prolapse," Am. J. Obstet. Gynecol., 1961, 81(2):281-290.
Certified priority document for GB Application No. 0025068.8, filed Oct. 12, 2000, 38 pages.
Certified priority document for GB Application No. 0208359.0, filed Apr. 11, 2002, 50 pages.
Certified priority document for GB Application No. 0411360.1, filed May 21, 2004, 31 pages.
Cheri, Biologic Grafts and Synthetic Meshes in Pelvic Reconstructive Surgery, Jun. 2007.
Choe and Staskin, "Gore-Tex Patch Sling: 7 Years Later," Urology, 1999, 54:641-646.
Chopra et al., "Technique of Rectangular Fascial Sling," Female Urology, 1996, Raz (ed.), W.B. Saunders Company, Chapter 34, pp. 392-394.
Churchill's Medical Dictionary (1989).
Dargent, D. et al., Pose d'un ruban sous uretral oblique par vote obturatrice dans le traitement de L'incontinence urinary feminine [English "Insertion of a transobturator oblique suburethral sling in the treatment of female urinary incontinence"], Gynecol. Obstet. Ferril. 14, pp. 576-582 (2002) [including English translation at the beginning of document].
Das and Palmer, "Laparoscopic Colpo-Suspension," J. Urol., 1995, 154:1119-1121.
De Leval, J., "Novel Surgical Technique for the Treatment of Female Stress Urinary Continence: Transobturator Vaginal Tape Inside-Out," European Urology, 2003, 44:724-730.
DeBord, James R., (1998), "The Historical Development of Prosthetics in Hernia Surgery," Surgical Clinics of North America, 78(6): 973-1006.
Decter, "Use of the Fascial Sling for Neurogenic Incontinence: Lessons Learned," J. Urol., 1993, 150:683-686.
Delmore, E. et al., La bandelette trans-obturatrice: Un procede mini-invasif pour traiter l'incontinence urinaire d'effort de la femme, Progres en Urologie, vol. 11, pp. 1306-1313 (2001) [including English translation at the beginning of document].
DeTayrac, et al. Prolapse repair by vaginal route using . . . Int. Urogynecol. J. (published online May 13, 2006).
Dwyer, Transvaginal repair of anterior and posterior compartment prolapse with Atrium polypropylene mesh, BJOG: An International Journal of Obstetrics & Gynaecology, Aug. 2004.
Enzelsberger et al., "Urodynamic and Radiologic Parameters Before and After Loop Surgery for Recurrent Urinary Stress Incontinence," Acta Obstet. Gynecol. Scand., 1990, 69:51-54.
Eriksen et al., "Lona-Term Effectiveness of the Burch Colposuspension in Female Urinary Stress Incontinence," Acta Obstet. Gynecol. Scand., 1990, 69:45-50.
Falconer et al., "Clinical Outcome and Changes in Connective Tissue Metabolism After Intravaginal Slingplasty in Stress Incontinent Women," Int. Urogynecol. J., 1996, 7:133-137.
Falconer et al., "Influence of Different Sling Materials on Connective Tissue Metabolism in Stress Urinary Incontinent Women," Int. Urogynecol. J., 2001, (Suppl. 2):S19-S23.
Gilja et al., "A Modified Raz Bladder Neck Suspension Operation (Transvaginal Burch)," J. Urol., 1995, 153:1455-1457.
Gittes and Loughlin, "No-Incision Pubovaginal Suspension for Stress Incontinence," J. Urol., 1987, 138:568-570.
Gruss, "The Obturator Bypass. Indications. Techniques. Outcomes," Chirurgie, 1971, 97:220-226.
Guida and Moore, "The Surgeon at Work. Obturator Bypass Technique," Surgery, Gynecology & Obstetrics, 1969, pp. 1307-1315.
Handa et al., "Banked Human Fascia Lata for the Suburethral Sling Procedure: A Preliminary Report," Obstet. Gynecol., 1996, 88:1045-1049.
Hardiman, et al. Cystocele repair using polypropylene mesh. Br. J. Obstet. Gynaecol. 107: 825-26 (2000).

(56) References Cited

OTHER PUBLICATIONS

Henriksson and Ulmsten, "A urodynamic evaluation of the effects of abdominal urethrocystopexy and vaginal sling urethroplasty in women with stress incontinence," Am. J. Obstet. Gynecol., 1978, 131:77-82.
Hodgkinson and Kelly, "Urinary Stress Incontinence in the Female. III. Round-ligament technique for retropubic suspension of the urethra," Obstet. Gynecol., 1957, 10:493-499.
Amended Answer and Counterclaim (Mar. 30, 2004) *American Medical Systems, Inc.* v. *Mentor Corporation*, Civ. No. 03/5759.
AMS's Reply to Mentor's Counterclaim (Apr. 5, 2004) *American Medical Systems, Inc.* v. *Mentor Corporation*, Civ. No. 03-CV-5759.
Answer and Counterclaim (Mar. 15, 2004) *American Medical Systems, Inc.* v. *Mentor Corporation*, Civ. No. 03-5759.
Answer and Counterclaim of American Medical Systems, Inc. (Mar. 11, 2004) *Mentor Corporation* v. *American Medical Systems, Inc.*, Civ. Case No. 04-1000 DWF/SRN.
Canepa, G. et al., "Horseshoe-shaped Marlex mesh for the treatment of pelvic floor prolapse," European Urology (Jan. 2001) 39 (Supl 2): 23-27.
Complaint and Jury Demand (Feb. 8, 2010), *Coloplast A/S* v. *Mpathy Medical Devices, Inc.*, Court File No. CV10-206.
Complaint for Declaratory Judgment (Oct. 28, 2003) *American Medical Systems, Inc.* v. *Mentor Corporation*.
Complaint for Patent Infringement (Feb. 20, 2004) *Mentor Corporation* v. *American Medical Systems, Inc.*
Complaint for Patent Infringement and Exhibits (Feb. 8, 2010) *Coloplast A/S*, v. *Generic Medical Devices, Inc.*, Court File No. CV10-227 BHS.
Cook, Urogynecology, Product Technical Datasheet and Order form, 1996.
D. Elliott Declaration and Attachment 1 (Jan. 5, 2011) *Coloplast A/S*, v. *Generic Medical Devices, Inc.*, Court File No. CV 10-227 BHS.
Declaration of Dr. George D. Webster in Support of Generic Medical Devices, Inc.'s Briefing on Claim Construction and Exhibits for *Coloplast A/S*, v. *Generic Medical Devices, Inc.*, Court File No. CV 10-227 BHS, signed Jan. 5, 2011.
Declaration of Jeya Paul and Attachment 1 (Jan. 10, 2011) *Coloplast A/S*, v. *Generic Medical Devices, Inc.*, Court File No. CV 10-227 BHS.
Declaration of Marc Belloli in Support of GMD's Opening Claim Construction Brief and Exhibits A-J (Jan. 10, 2011) *Coloplast A/S* v. *Generic Medical Devices, Inc.*, Court File No. CV 10-227 BHS.
Generic Medical Devices, Inc.'s Answer to Complaint and Counterclaims (Mar. 1, 2010) *Coloplast A/S*, v. *Generic Medical Devices, Inc.*, Court File No. CV10-227 BHS.
Generic Medical Devices, Inc.'s Non, Infringement and Invalidity Contentions and Accompanying Document Production (Aug. 9, 2010) *Coloplast A/S*, v. *Generic Medical Devices, Inc.*, Court File No. CV-I0-227 BHS.
Generic Medical Devices, Inc.'s Opening Claim Construction Brief (Jan. 10, 2011) *Coloplast A/S*, v. *Generic Medical Devices, Inc.*, Court File No. CV10-227 BHS.
International Preliminary Examination Report issued in PCT/GB2002/001234, completed Jul. 1, 2003, 18 pages.
International Search Report and Written Opinion issued in PCT/US03/24212, dated May 28, 2004, 11 pages.
International Search Report issued in PCT/GB2002/01234 dated Jun. 5, 2002, 3 pages.
Joint Claim Construction and Preheating Statement Pursuant to Local Patent Rule 132 and Appendix A (Nov. 15, 2010) *Coloplast A/S*, v. *Generic Medical Devices, Inc.*, Court File No. CV10-227 BHS.
Migliari, R. et al., "Tension-Free Vaginal Mesh Repair for Anterior Vaginal Wall Prolapse," European Urology (2000) 38(2): 151-155.
Order dismissing cases (Sep. 16, 2004) Civ. No. 03-5759 and Civ. No. 04-1000.
Parker, MC and Phillips, RK, "Repair of rectocoele using Marlex mesh," Ann R Coll Surg Engl (May 1993) 75(3): 193-194.
Plaintiff Coloplast ,A/S's Opening Claim Construction Brief (Jan. 10, 2011) *Coloplast A/S*, v. *Generic Medical Devices, Inc.*, Court File No. CV 10-227 BHS.
Plaintiff Coloplast A/S's Answer to Defendant Generic Medical Devices, Inc.'s Counterclaims (Mar. 22, 2010) *Coloplast A/S*, v. *Generic Medical Devices, Inc.*, Court File No. CV10-227 BHS.
Plaintiff Coloplast A/S's Disclosure of Asserted Claims and Infringement Contentions (Jul. 6, 2010) *Coloplast A/S*, v. *Generic Medical Devices, Inc.*, Court File No. CV '10-227 BHS.
Plaintiff's Reply to Counterclaim (Mar. 30, 2004) *Mentor Corporation* v. *American Medical Systems, Inc.* (Civ. No. 04-1000).
Sand et al., "Prospective randomized trial of polyglactin 910 mesh to prevent recurrence of cystoceles and rectoceles," American Journal of Obstetrics & Gynecology vol. 184, Issue 7, pp. 1357-1364, Jun. 2001.
Scheffini, M. et al., "Abdominal sacral colpopexy with prolene mesh," Int Urogynecol J Pelvic Floor Dysfunct (1999) 10(5): 259-299.
Supplemental European Search Report issued in EP Application No. 03751825, dated Jun. 19, 2009, 5 pages.
U.S. Appl. No. 60/327,160, filed Oct. 4, 2001.

\* cited by examiner

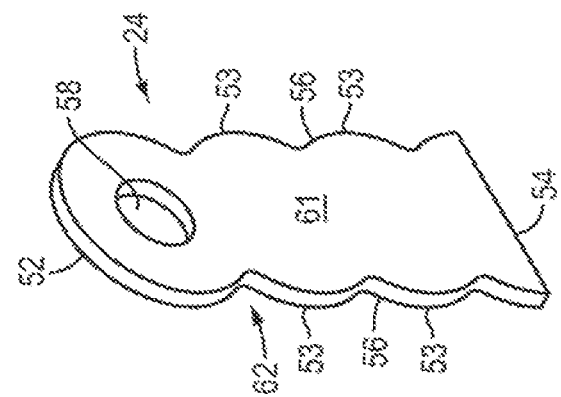
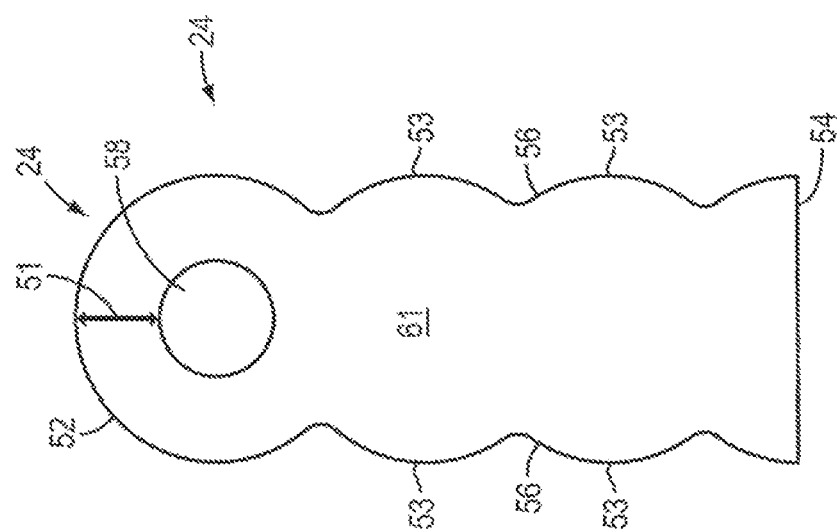
FIG. 3B
FIG. 3A

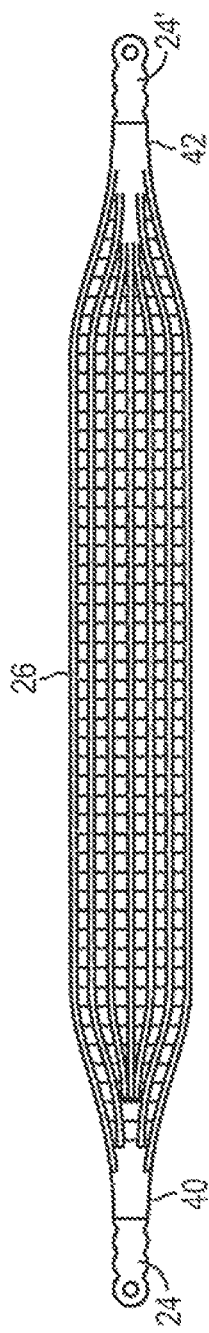
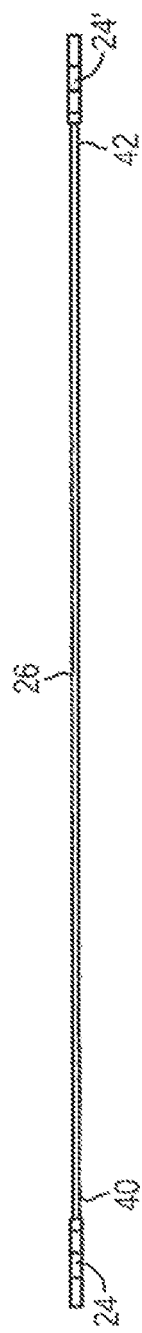
FIG. 5A
FIG. 5B

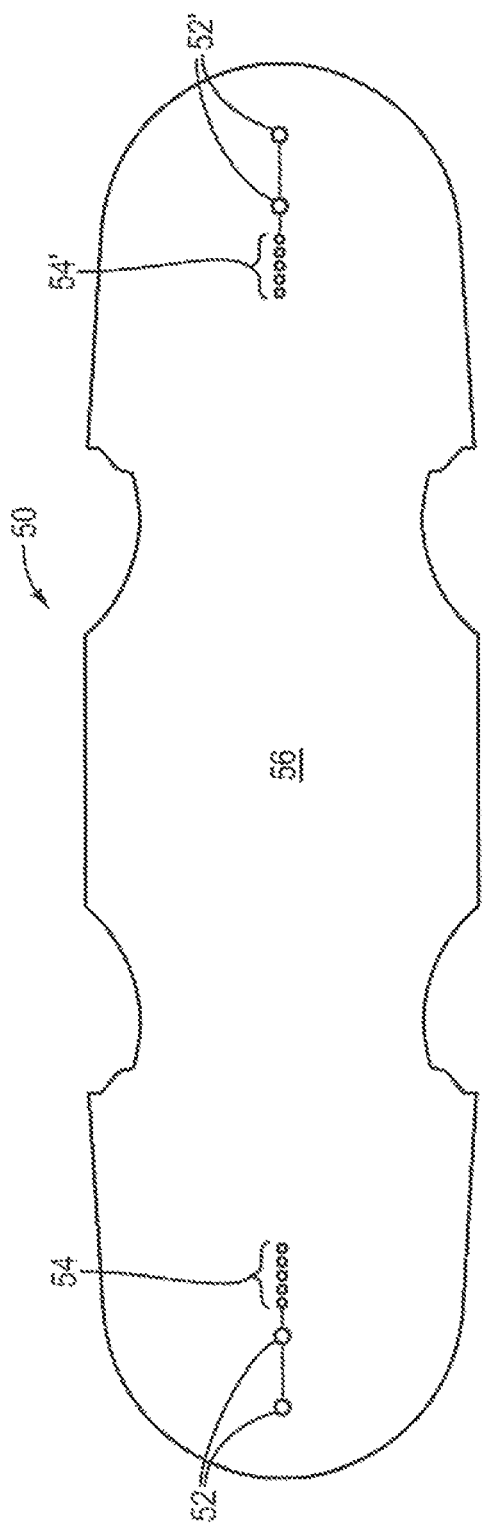
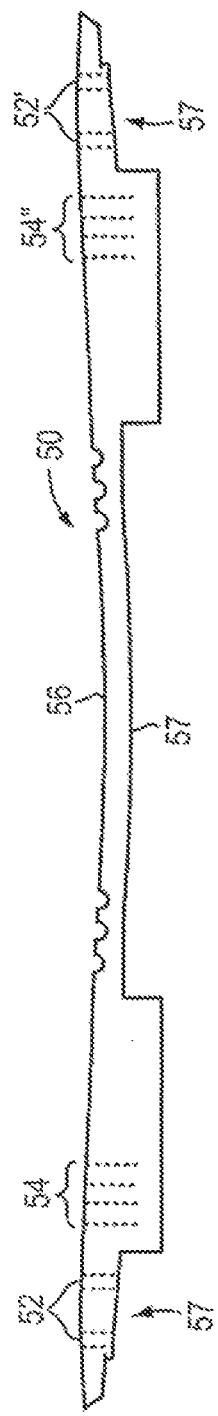
FIG. 6A
FIG. 6B

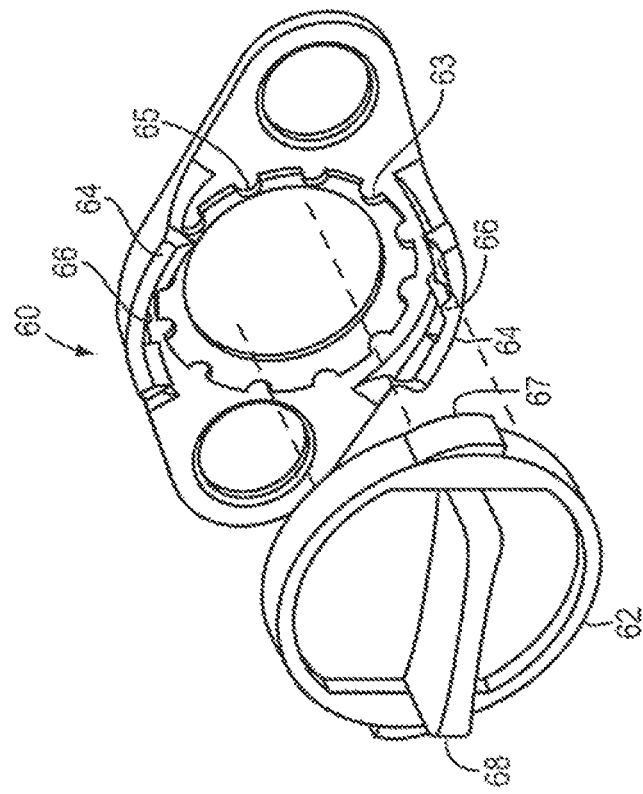
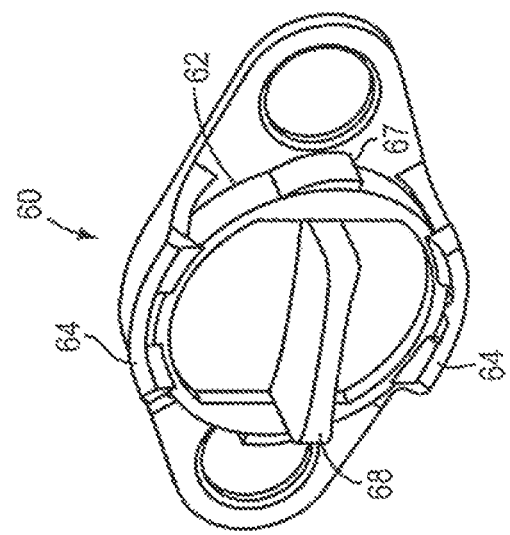

METHOD OF POST-OPERATIVELY ADJUSTING A URETHRAL SUPPORT IN TREATING URINARY INCONTINENCE OF A WOMAN

CROSS REFERENCE TO RELATED APPLICATIONS

This application is a continuation of U.S. Ser. No. 14/151,873 filed Jan. 10, 2014 and now issued as U.S. Pat. No. 9,089,394, which is a continuation of U.S. application Ser. No. 13/402,978 filed Feb. 23, 2012 and now issued as U.S. Pat. No. 8,668,635, which is a continuation of U.S. application Ser. No. 12/072,901 filed Feb. 28, 2008 and now issued as U.S. Pat. No. 8,167,785. Priority to each of the foregoing is claimed.

TECHNICAL FIELD

This invention relates to a system and method for the treatment of pelvic floor abnormalities, in particular female urinary incontinence.

BACKGROUND OF THE INVENTION

Urinary incontinence is an involuntary release of urine when increases in abdominal pressure caused by sneezing, coughing, or exercising, for example, are not uniformly transmitted to the proximal urethra, resulting in urine "leakage." Moderate urinary incontinence is inconvenient and can be a social and hygienic problem, while severe urinary incontinence can be disabling. Urinary incontinence occurs in women and is caused by for example, hypermobility of the bladder neck and proximal urethra (excessive downward and rotational movement of the bladder neck) or intrinsic sphincter deficiency.

Urinary incontinence affects a large number of women and, consequently, various approaches have been developed to treat female urinary incontinence. Those skilled in the art will be familiar with approaches ranging from pelvic floor exercises to surgical techniques such as Burch colposuspension and Stamey type endoscopic procedures in which the sutures are placed so as to elevate the bladder neck.

One known procedure positions a support, i.e., a sling loosely under the urethra. It is generally understood that this treatment alleviates urinary incontinence by occluding the mid-urethra (for example at a time of raised abdominal pressure by coughing or the like).

Problems associated with surgical correction of the failed support mechanisms include under-correction or over-correction. The surgeon must determine the degree of support necessary to properly elevate and support the urethra to properly address the urinary incontinence problem. This determination must be made both pre-, intra-, and post-operatively. Too little elevation causes urinary incontinence to remain, although the degree of incontinence may be reduced. Too much elevation can result in voiding dysfunction (reduced capacity or inability to void), leading to prolonged catheterization, and the need for postoperative correction.

The incidence of postoperative urinary retention due to post-operative obstruction can be high at several weeks after surgery, and a number of patients have post-operative urinary retention that persists. Symptomatic detrusor instability represents the bladder's response to increased outlet resistance caused by an improperly tensioned sling. The incidence of post-operative irritative symptoms secondary to detrusor instability can be unacceptably high. Appropriate tensioning of the suburethral support, i.e., sling minimizes persistent incontinence and voiding dysfunction. However, appropriate tensioning during surgery is difficult to assess and frequently is found to be excessive or insufficient once the patient has assumed normal posture and movement post-operatively. Methods and devices for immediate and short term post-operative adjustment of the tension in a suburethral support member, i.e., sling for the treatment of urinary incontinence are needed to mitigate the post-operative complications associated with inappropriate tensioning of the sling.

SUMMARY OF THE INVENTION

One of the problems identified and solved by the invention disclosed herein is that appropriate immediate and short-term post-operative tensioning of a suburethral support in a patient can minimize the discomfort, persistent incontinence and voiding dysfunction that often complicates prior art methods and devices for therapy of pelvic floor abnormalities including urinary incontinence. The invention described below relates to a system and method that permits fine tuning of a urethral support member, i.e., sling tension immediately post-operatively and for days up to a week rather than hours after the sling has been implanted in the patient. Accordingly, at least one objective according to the invention described herein is to provide a system and method that mitigates the post-operative complications associated with under-tensioning or over-tensioning a suburethral sling implanted for the therapy of urinary incontinence or other pelvic floor dysfunctional or structural abnormalities.

In one aspect, the invention relates to a supplementary stabilization system for stabilizing the urethra. The stabilization system has a first elongate thread member and a second elongate thread member, each elongate thread member comprising an absorbable, flexible material having a length extending from a first end to a second end. In one embodiment, the second end of each thread member is free. The system for stabilizing the urethra also has a first stabilizer and a second stabilizer. In one embodiment, the first stabilizer is joined to the first end of the first elongate thread member. The second stabilizer is joined to the first end of the second elongate member thread member.

In one embodiment, the elongate thread members are non-porous, i.e., having no interstices such as pits, gaps or holes for cellular integration. The width of each elongate thread member is in the range of 0.1 to 2 mm.

The supplementary stabilization system also has a first and second suspending member and a support member. The support member has a first end and a second end. The first suspending member and the second suspending member each have a first end and a second end. The first end of each suspending member is joined to one of the first or second stabilizer. The second end of each suspending member is joined to either the first end or the second end of the support member.

In one embodiment, the support member has a length that is shorter than either of the first and second thread member. In one embodiment, the first thread member and the second thread member have a width that is in the range of about 0.8% to 20% of the width of the support member. Each of the thread first thread member and the second thread member may also have a length that is longer than the support member.

In a particular embodiment, the urethral support system has a tensioner. The tensioner includes a mechanism for including and retaining 1 or 2 thread members and a mechanism for tightening and loosening the urethral support member by mechanically exerting a linear or rotary force movement or by manual means.

In another aspect, the invention relates to a method for stabilizing a urethral support member under the urethra to treat urinary incontinence, for example. According to the method, a surgeon introduces a urethral support stabilization system including an absorbable first elongate member and an absorbable second elongate member having a first end and a second end, and the urethral support member through an incision in the vaginal wall. The first end of the system is introduced to the paraurethral space lateral to the urethra, through the subcutaneous tissue, and through the skin at a first location. The second end of the system is introduced in the paraurethral space on the other side of the urethra, through the subcutaneous tissue on that side of the urethra, and through the skin at a second location. In one embodiment the first and second locations are located on the skin of the abdomen. In another embodiment, the first and second locations are located on the perineal skin or the skin of the upper medial leg.

In an alternative method, the order of tissues through which the urethral support system passes is reverse of the order above.

In one embodiment, the urethral support stabilization system further includes a stabilizer connectable to an elongate member. The method further comprises positioning the stabilizer in soft tissue, for example, in the soft tissue of the retropubic space, the soft tissue of the perineal space, or the pre-pubic soft tissue. The stabilizer is located between an absorbable elongate member and the urethral support member. The length of the urethral support stabilization system between the stabilizer and the midpoint of the urethral support member is less than the distance between the patient's urethra and the skin at the first location. According to the invention, the stabilizer is positioned in pelvic soft tissue without penetrating the rectus sheath, in a vaginal to abdominal approach, or the subcutaneous tissue of the perineal skin in a vaginal to perineal approach or in the subcutaneous tissue of the pre-pubic skin in a vaginal to pre-pubic approach.

In one embodiment, the method of the invention further includes providing a tensioner to the surface of the abdominal perineal, or pre-pubic skin, as the case may be. The tensioner has a first and second end and is joined to the first and second elongate members, respectively, after the elongate members emerge from the skin. The method further includes adjusting the tension on the support member by adjusting the tensioner. At anytime up to ten days after the urethral support member is implanted in the patient, tension is applied to the second end of the elongate member at the first location. In one embodiment, the tension is applied manually by the surgeon. Alternatively, tension may be applied to the elongate member and transmitted to the urethral support member by mechanical means, for example, by a mechanical rotary or a linear force movement. The magnitude of the tension is sufficient to permit a remnant of the first end of the elongate member to retract under the skin after cutting the remnant. The first end of the elongate member is cut while it is under tension wherein the remnant of the first end retracts under the skin.

In one embodiment of the method of the invention, applying tension to one or the other elongate member comprises advancing or withdrawing one or the other stabilizer in the soft tissues of the patient. As used herein, withdrawing a stabilizer in the soft tissues of the patient means moving the stabilizer back along the path in which the stabilizer was advanced, i.e., in a reverse direction, without causing significant trauma to the soft tissue along the path and without applying more force, preferably less force, than the force that was required to advance the stabilizer.

These and other objects, along with advantages and features of the present invention herein disclosed, will become apparent through reference to the following description, the accompanying drawings, and the claims. Furthermore, it is to be understood that the features of the various embodiments described herein are not mutually exclusive and can exist in various combinations and permutations.

BRIEF DESCRIPTION OF THE FIGURES

The foregoing and other objects, features and advantages of the present invention disclosed herein, as well as the invention itself, will be more fully understood from the following description of preferred embodiments and claims, when read together with the accompanying drawings. The drawings are not necessarily to scale, emphasis instead generally being placed upon illustrating the principles of the invention.

FIG. 3A illustrates a front view and FIG. 3B illustrates a perspective view of a stabilizer of the urethral support system according to an embodiment of the invention;

FIG. 5A illustrates a top view of a urethral support member connected to a stabilizer at each end of the urethral support system according to an embodiment of the invention;

FIG. 5B illustrates a side view of the urethral support member and stabilizer illustrated in FIG. 5A;

FIG. 6A illustrates a top view of a tensioner of the urethral support system according to an embodiment of the invention;

FIG. 6B illustrates a side view of the tensioner illustrated in FIG. 6A;

FIG. 7A illustrates a perspective view of a tensioner of the urethral support system according to another embodiment of the invention;

FIG. 7B illustrates an exploded view of the tensioner illustrated in FIG. 7A;

DESCRIPTION

Figure 1:
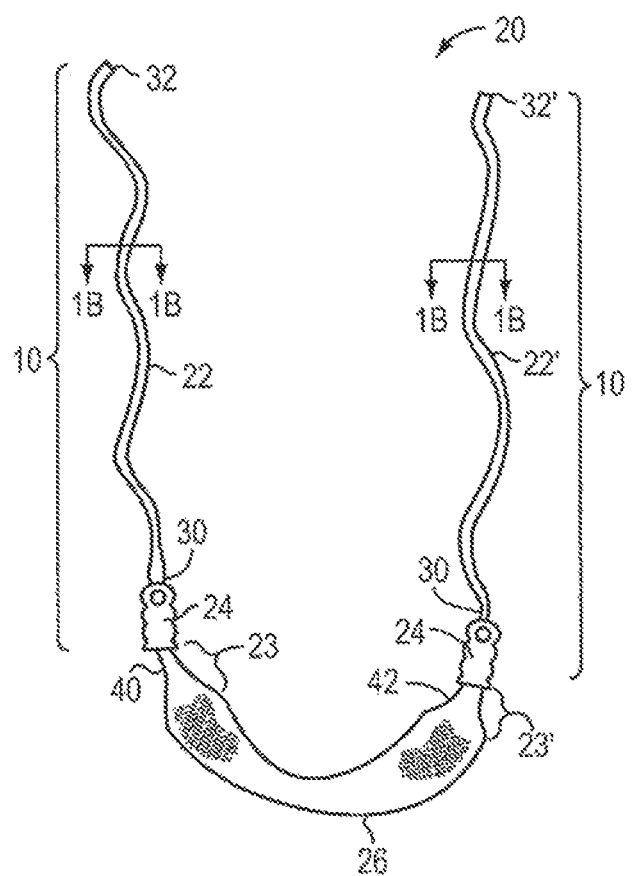
FIG. 1 illustrates a plan view of a urethral support system according to an embodiment of the invention.

FIG. 1 illustrates a urethral support system 20 according to an embodiment of the invention. Referring to FIG. 1, the exemplary urethral support system 20 has multiple components including a supplementary urethral support stabilization system 10 comprising a first elongate member 22 and a second elongate member 22'. In one embodiment of the invention, the supplementary urethral support stabilization system 10 further includes at least one tensioner (not shown), alternatively two tensioners described below. In another embodiment, the supplementary stabilization system 10 includes a first elongate member 22 and a second elongate member 22', and a first stabilizer 24 and a second stabilizer 24'. Alternatively, the supplementary urethral support stabilization system 10 includes at least one tensioner, a first and second elongate member 22, 22', and a first and second stabilizer 24, 24'. The urethral support system 20 further includes a support member 26. In one embodiment, the urethral support system 20 further includes a first suspending member 23 and a second suspending member 23'.

Figure 2B:
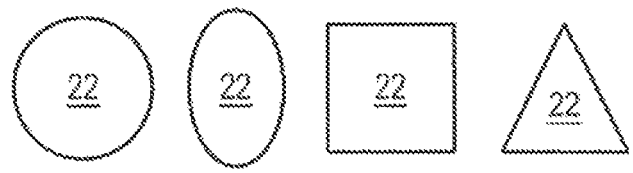
FIG. 2B illustrates various embodiments of the cross-sectional shape of the first and second elongate members taken at 1B-1B of the urethral support system illustrated in FIG. 1.
Figure 2A:
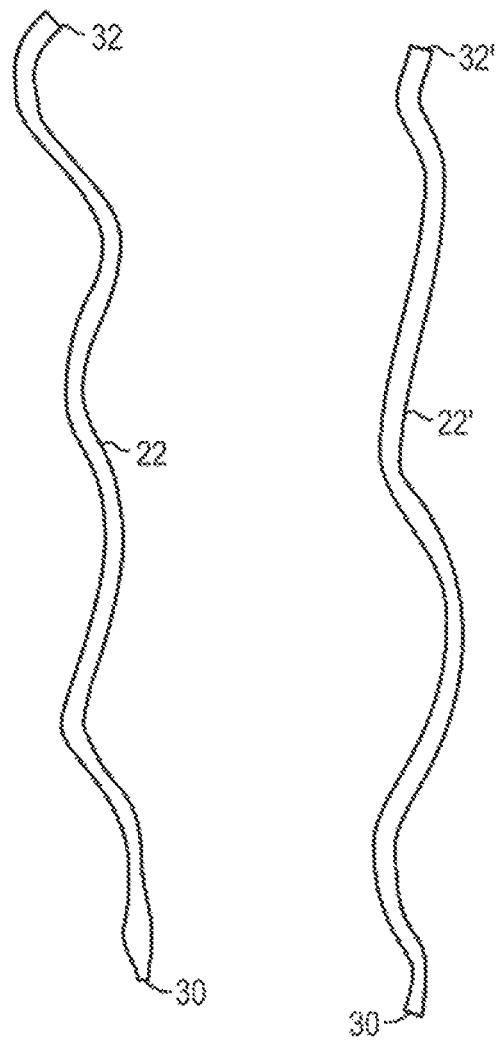
FIG. 2A illustrates a side view of a first elongate member and a second elongate member of the urethral support system according to an embodiment of the invention.

FIGS. 2A and 2B illustrate an embodiment of the supplementary urethral support stabilization system 10 of the urethral support system 20 including the first elongate member 22 and the second elongate member 22'. With reference to FIG. 2A, the exemplary first elongate member 22 and the exemplary second elongate member 22' are substantially identical and typically thread-like, i.e., not tape or ribbon-like members. The material used to make the elongate member is absorbable, i.e., biodegradable and does not act as a scaffold to permit ingrowth of patient tissues, e.g., fibrous tissue, into the material. Appropriate materials include absorbable synthetic polymers, lactide, glycolide, caprolactone, co-polymers or combinations of the above, for example. In one embodiment, the material used to make the elongate member is solid, for example, monofilament without interstices such as pores, pits, or spaces, for example, that would permit cellular integration in the material, i.e., not a mesh, braid, knitted, or woven material. In another embodiment the material may be braided.

Each of the first elongate member 22 and the second elongate member 22' is longer or as long as the urethral support member 26 (described below in greater detail). Embodiments of the elongate member made from a monofilament lack the projecting ends of mesh, knitted, woven, or braided materials and therefore slide in soft tissue more easily forward (advancing) in one direction or backward (withdrawing) in the opposite direction. In one embodiment, each of the first elongate member 22 and the second elongate member 22' includes a first end 30 and a second end 32. In one embodiment, the second end 32 is free while the first end 30 is joined to another part of the urethral support system 20.

Referring to FIG. 2B, typically, the first elongate member 22 and second elongate member 22' of the supplementary urethral support stabilization system 10 have a cross-sectional width in the range of about 0.1 to 2.0 millimeters. The cross-sectional shape of the first 22 and second elongate members 22' may be round, oval, triangular, or rectangular, for example. In one embodiment, the thread-like elongate members 22, 22' are sufficiently flexible to be knotted. The elongate members may be coated with an absorbable, i.e., biodegradable lubricious material, for example, proteins, polysaccharides, hydrophilic polymers, wax, hydrogel, silicone, silicone rubber, PTFE, PBA, ethyl cellulose or the like, to ease the sliding of the elongate member in soft tissues. The length of each of the first and second elongate members is in the range for example of about, 6-18 cm, preferably 7-16 cm. The thin, thread-like feature of the elongate member is advantageous over the prior art because the elongate members according to the invention do not permit ingrowth of patient tissue and slide in two-directions, i.e., forward and backward more easily than prior art urethral support sling systems which use broad flat tape-like members to encourage ingrowth of patient tissues and can not be moved without causing significant tissue trauma after operative placement.

FIGS. 3A and 3B illustrate an exemplary stabilizer 24 of the supplementary urethral support stabilization system 10 of the urethral support system 20 according to an embodiment of the invention. Referring to FIG. 3A, the exemplary stabilizer 24 is a planar, elongate, substantially rectangular or oval tab including a radius 51 at the distal end 52, and is flat at the proximal end 54 opposite to the distal end 52. Alternatively, the stabilizer 24 is substantially cylindrical (not shown) rather than planar or the stabilizer 24 may include a radius 51 at the proximal end 54 as well as at the distal end 52. The sides 56 of the stabilizer 24 include multiple radii 53, or flat beads, for example, 2-6 flat beads, more preferably 1-2 flat beads, most preferably one bead, i.e., radius. Other than the "beads", all sides of the stabilizer are devoid of projections that may increase the drag or prevent substantially free passage of the stabilizer 24 in soft tissue. The length of the stabilizer 24 is in the range of about 0.8 to 2.0 cm. The width of the stabilizer at its widest point is in the range of about 2 to 4 mm, preferably 3 mm. The thickness of the stabilizer is in the range of about 100 to 400 microns, preferably 200 microns.

With continued reference to FIGS. 3A and 3B, in one embodiment of the invention, the illustrated exemplary stabilizer 24 includes a throughhole 58 at the distal end 52 extending from one surface 61 to the other surface 62 of the stabilizer 24. In one embodiment, the throughhole 58 operates as an eyelet to which the first end of the elongate member (not shown) may be knotted to connect the stabilizer to the elongate member. The multiple beads 53 along the sides 56 of the stabilizer 24 permit ratcheting of the stabilizer 24 as it is pulled through the fascia of the patient by the surgeon during implantation of the urethral support system 20 illustrated in FIG. 1. Ratcheting aids the surgeon during the implantation procedure by increasing the "feel" of the system as it is being implanted.

The stabilizer 24 including the beads along the sides, described above, has at least one advantage over prior art stabilizers in that the stabilizer 24 may be reversibly transitioned in tissue, i.e., movement in tissues two-ways: (i) forward along the path of the respective elongate member to which the stabilizer 24 is joined, and (ii) back along the path already taken by the stabilizer 24. Accordingly, the stabilizer 24 permits positional fine-tuning by transitioning the stabilizer 24 forward or backwards, for example, by pulling in either direction during and after delivery of the urethral support system 20 in the patient's tissues. Moreover, the stabilizers of the supplementary stabilization system 10 aid in holding the urethral support member under the urethra in a correct position. In addition, the stabilizers according to the invention are not readily palpable, or may not be palpable transvaginally. The stabilizers and/or the supplementary stabilization system, according to the invention, are positioned in the soft tissue with adequate tensile strength to counter dislodging by, for example, coughing or straining, or by other instances of increased intra-abdominal pressure, until suitable integration of the patient's soft tissue occurs with the implanted urethral support member. Typically, the timeframe required for integration of the urethral support member is about 24 hours to about seven days.

The stabilizer according to the invention differs structurally and functionally from prior art devices because prior art devices are typically pronged, barbed, or have rough surfaces that, once drawn into soft tissue, cannot be withdrawn along the path already taken by the device. In contrast, the stabilizer according to the invention may be withdrawn along the tissue path already taken with minimal trauma to the soft tissue and allows forward and backward repositioning of the urethral support member. In particular, the stabilizer according to the invention permits adjustment to the tension of the urethral support member by transmitting the tension to the urethral support member through the stabilizer after the stabilizer is introduced into the patient's tissues. Because the stabilizer can be moved forward (advanced) and backward (withdrawn), tension transmitted to the urethral support member can be reduced as well as increased, a feature not present in prior art urethral support systems or methods for treating urinary incontinence.

Referring again to FIG. 1, the exemplary first stabilizer 24 is joined to the first end 30 of the first elongate member 22 and the second stabilizer 24' is joined to the first end 30 of the second elongate member 22' of the supplementary urethral support stabilization system 10. The stabilizer may be joined to the elongate member by any means known in the art, such as by knotting the elongate member to the stabilizer through the stabilizer throughhole, for example, or by thermal bonding, ultrasonic bonding, application of an adhesive, chemical bonding, or by molding a stabilizer-elongate member combination such that the stabilizer and the elongate member form a single integral part.

Figure 4:
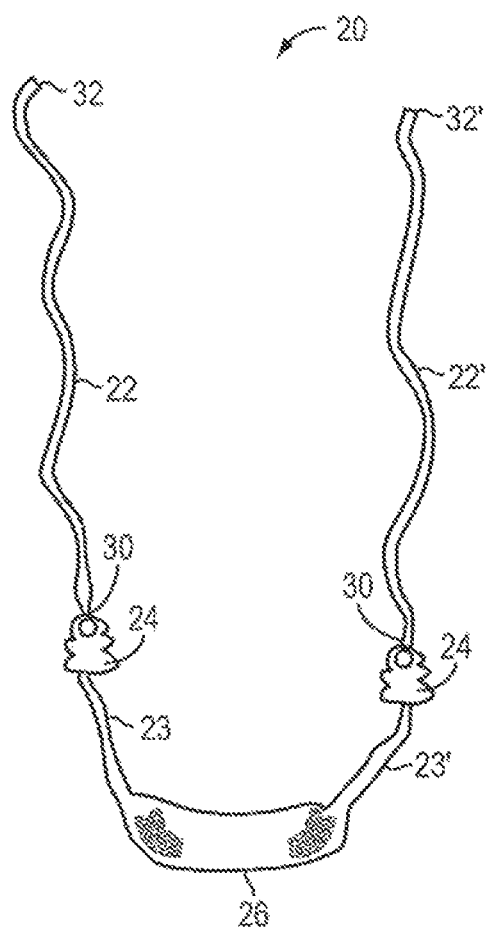
FIG. 4 illustrates a plan view of a urethral support system including a first suspending member and a second suspending member according to another embodiment of the invention.

Referring to FIG. 4, in one embodiment, the urethral support system 20 further includes a first suspending member 23 and a second suspending member 23' that connect the first stabilizer 24 to one end of the urethral support member 26, and the second stabilizer 24' to the other end of the urethral support member, respectively. The suspending members 23 may be for example, a strip, such as, for example, a polymer strip. The suspending members may be joined to the support member 26 and/or the stabilizers 24, 24' by crimping, thermal bonding, chemical bonding, ultrasonic bonding, adhesive, or formed as an integral unit with the stabilizers and or the urethral support member.

Each of the exemplary first suspending member 23 and second suspending member 23' illustrated in FIG. 4 feature an elongated element having a length in the range of about 1 to 3 cm, preferably about 1 to 2 cm. The width of each of the suspending members is typically 11 mm on the end adjacent to the mesh tapering to 2 mm on the end adjacent to the stabilizer.

In another embodiment referring again to FIG. 1, the exemplary suspending members 23, 23' form an integral part of the urethral support member 26 and taper to the stabilizers 24, 24', respectively. Alternatively, the urethral support member 26 is joined directly to the stabilizers 24, 24' without an intervening suspending member (see FIGS. 5A-5B).

FIGS. 5A and 5B illustrate a urethral support member 26, such as a sling, according to an embodiment of the invention. The exemplary urethral support member 26 is a flat, ribbon, or tape-like implant. According to one embodiment, the support member 26 is a mesh comprised of strands. The length of the support member 26 is in the range of about, 6 to 20 cm, preferably 7 to 16 cm, more preferably 8 to 14 cm preferably 12 cm, or 8 cm in length. The width of the urethral support member 26 may be in the range of about 6 to 15 mm, preferably 8 to 13 mm, more preferably 11 mm in width. The weight of the urethral support member 26 is in the range of about 10 to 30 g/m$^2$, preferably 15 to 25 g/m$^2$, more preferably 18 to 20 g/m$^2$, most preferably 19 g/m$^2$. Exemplary embodiments of the mesh urethral support member are described in U.S. Ser. Nos. 10/473,825 and 10/398,992, incorporated by reference herein. The strands of the mesh urethral support member 26 are in the range of about 150 to 600 microns in diameter. The strands are arranged such that they form a regular network and are spaced apart from each other such that for a diamond net arrangement a space of between 2 to 5 mm exists between the points where the strands of the mesh interact with each other. In a hexagonal net arrangement the space is between 2 to 5 mm between opposite diagonal points where the strands of the mesh interact.

It is preferable to space the strands as far as part as possible to allow blood to pass through the implant and reduce the mass of the implant, while providing the mesh with sufficient tensile strength and elasticity to be effective. It can therefore be appreciated that considerable variability in the maximum spacing between the strands can be achieved depending on the material from which the strands are comprised and the net pattern in which the strands are arranged.

In one embodiment the strands are arranged in a diamond net pattern, however any pattern which provides suitable tensile strength and elasticity may be used. For example a hexagonal net pattern may be used.

Ideally, in order to reduce the overall mass of the urethral support member, the strands should have as narrow a diameter as possible while still providing the mesh with suitable tensile strength and elasticity. The strands of the mesh include at least two filaments arranged to interact such that pores are formed between the filaments. The pores formed between the filaments are around about 50 to 200 microns, such a spacing allowing fibroblast through growth to occur. Fibroblast through growth secures the implant in place within the body. Additionally and importantly the suitably sized pores allow the implant to act as a scaffold to encourage the deposition of new patient tissue to promote integration of the urethral support member into the patient's soft tissues.

Suitable materials from which the mesh can be made are sufficiently inert to avoid foreign body reactions when retained in the human body for long periods of time and have suitably easy handling characteristics for placement under the urethra in the desired location in the body. The mesh can be easily sterilized to prevent the introduction of infection when the mesh is implanted in the human body.

For example, the filaments may be formed from any biocompatible material. In one embodiment, the filaments are formed from polyester, wherein each polyester filament is around 0.09 mm in diameter. Suitable materials of which the filaments may be formed also include polypropylene.

The filaments of the strands may be knitted together using warp knit to reduce the possibility of fraying of the filaments and strands. The fine warp knit of the filaments provides a urethral support member which is flexible in handling, which can be easily cut into different shapes and dimensions. As the strands are formed using warp knit, the possibility of fraying of the edge of the urethral support member following production or cutting of the mesh is reduced.

Other methods of reducing fraying of the filaments after cutting or production of the mesh include heat treatment, laser treatment or the like to seal the edges of the mesh.

The mesh may be supplied in any shape or size and cut to the appropriate dimensions as required.

It can be appreciated that cutting of the mesh will produce an unfinished edge. Due to the sparse nature of the strands that form the mesh and their narrow diameter, this unfinished edge does not suffer from the same problems as edges of meshes of the prior art.

In other words the edge produced is not rough and jagged such that it increases the likelihood of extrusion of the edge of the mesh in situ or the chance of infection.

An advantage of the mesh of the present invention is that it allows substantially less foreign material to be left into the body than conventional meshes for pelvic region repair.

However, to improve handling the mesh described above may be treated using an absorbable coating. The absorbable coating includes, for example, a layer of absorbable material having a thickness greater than that of the strands of the mesh. For example, the thickness of the layer of absorbable material may be around 1 to 2 mm. The strands of the mesh may be entirely embedded in the absorbable coating such that the outer surface of the mesh is covered entirely of the absorbable coating encasing the entire urethral support member.

Accordingly, in this embodiment, urethral support member has no gaps or holes on its surface to reduce the likelihood of bacteria becoming lodged on the strands of the mesh before implantation of the mesh. Furthermore, the absorbable coating makes the mesh more substantial and less flexible such that it is more easily handled by a surgeon.

In an alternative embodiment, the absorbable coating includes a layer of absorbable material applied to one face of the mesh, such that the mesh has a first face on which the absorbable material has been applied and a second face on which the absorbable material has not been applied such that the first and second faces and each have different characteristics.

It can also be envisaged that the surgical implant is provided with improved surgical handling qualities by a range of other methods. Such methods include the releasable attachment of the mesh to a backing strip.

The backing strip may be formed from plastics material and is adhered to the surgical implant using releasable adhesive.

In a similar fashion to the absorbable coating the backing strip causes the mesh to be more substantial and less flexible such that it is more easily handled by a surgeon. Following the suitable placement of the mesh the backing strip can be removed from the mesh, the mesh being retained in the body and the backing material being removed by the surgeon. Application of the backing strip to the mesh means the mesh benefits from reduced mass but that the mesh and backing strip together give characteristics required for surgical handling.

In a further embodiment, the filaments of the mesh may be comprised from bicomponent microfibres or composite polymers. These technologies provide the implant with dual phase technology.

The bicomponent microfibres comprise a core and surface material. The surface material may be resorbed by host tissues in a matter of hours, while the core material remains in the body for a longer period to enable tissue ingrowth.

Suitable bicomponent microfibres include a polypropylene non-absorbable portion and a polylactic acid absorbable portion, for example.

The surface material is present during the surgical procedure when the mesh is being inserted and positioned in the soft tissues of the patient, and provides the mesh with characteristics desirable for surgical handling. Following implantation in the patient's body, typically a few hours, the surface material is absorbed by the body leaving only the core material of the filaments in the body. The core material of the filament has reduced foreign mass in comparison to meshes of the prior art or the mesh when it also includes the surface material.

The mesh of the urethral support member may be formed from composite polymers. As described for the bicomponent microfibres, composite polymers provide the urethral support implants with dual phase technology. A first face of the mesh has particular characteristics such as flexibility and elasticity, while a second face of the mesh provides the mesh with characteristics which improved the surgical handling of the mesh such as strength and robustness. The mesh results in an unfinished edge. This mesh is not as likely to cause the same problems as the rough and jagged edges of the of prior art mesh, due to the fewer strands, smaller diameter filaments and treatment of the mesh with absorbable coating which protects the tissue from the mesh during implantation when damage is most likely to occur.

In a further embodiment, the mesh has perimeter strands. Typically, the mesh is circular or the like in shape and thus the perimeter strand can be generally referred to as a circumferential strand. One strand runs around the circumference of the oval shape of the mesh. In another embodiment, several circumferential strands may be present, each circumferential strand may extend over one side of the oval mesh, i.e. around half the circumference of the mesh. In another embodiment, the circumferential strands arc arranged concentrically and each extends around the mesh at a different radial location.

An outer circumferential strand extending around the perimeter of the mesh, and further circumferential strands are arranged inwardly of the outer circumferential strand forming a perimeter spaced by a distance. The distance between adjacent circumferential members, can vary and in this example is 20 mm.

Transverse strands extend from the centre of the oval mesh to points on the perimeter of the mesh. In this example, four transverse strands are provided across the diameter of the mesh, dividing the mesh into eight angularly equal portions.

The mesh of this embodiment may be formed from materials as previously described. Depending on the material chosen the mesh may be woven, knitted or extruded as one piece, or individual or groups of strands can be extruded separately and joined to one another.

In another embodiment, meshes may have angled sides. A mesh according to this embodiment has a similar structure to that described above. However, the mesh has a perimeter member having angled sides. Further it may have transverse members arranged only to extend towards the perimeter of the mesh, rather than all being across the diameter of the mesh. This provides a more uniform structure. More specifically, the mesh has a transverse member extending along its axis of symmetry, a transverse member bisecting the axis of symmetry, and four further transverse members extending from the axis of symmetry to the perimeter of the mesh.

In addition to the pores provided by the combination of filaments which form the strands, pores can be provided by rings of polypropylene positioned at the intersection of the circumferential and transverse members.

Alternatively the pores may be formed by the spacing of the transverse members, such that pores of a size 50 to 200 microns suitable for enabling tissue ingrowth between the transverse members.

With continued reference to FIGS. 5A and 5B, the urethral support member 26 has a first end 40 and a second end 42. In one embodiment, the length of the urethral support member 26 is shorter than the length of either of the first elongate member 22 and second elongate member 22'. For example, the length of the urethral support member 26 is about 5-100%, preferably about 5-60%, more preferably, 5-30%, most preferably 5-20%, of the length of either the first elongate member 22 or the second elongate member 22'. The width of each elongate member may be in the range of about 0.1-30%, 0.8-20%, 1-20%, or 5-10% of the width of the urethral support member, for example.

Referring still to FIGS. 5A and 5B, in one embodiment, the first end 40 of the urethral support member 26 is joined to the first stabilizer 24, and the second end 42 of the urethral support member 26 is joined to the second stabilizer 24'. The end of the support member may be attached to either the first or second stabilizer by ultrasonic welding, thermal bonding, chemical bonding, an adhesive, or by a mechanical means such as, a fastener, a hook and eye, suture, and post and slot, for example. The attachment of the ends of the support member to the first or second stabilizer may be permanent or reversibly attached.

Referring to FIGS. 6A and 6B, in one embodiment according to the invention, the urethral support system 20 further comprises a tensioner 50. Any of the tensioners described herein may be reversibly attached to the patient's skin by, for example, an adhesive.

The exemplary tensioner 50 illustrated in FIGS. 6A and 6B typically is substantially flat to lie close to the skin thereby avoiding being inadvertently dislodged. The shape may be any suitable shape such as round, rectangular or oval as illustrated in FIG. 6A. The length of the tensioner is in the range of about 1 to 6 cm, preferably, 3 to 6 cm, 1 to 3 cm, or 1-4 cm. The width is in the range of about 1 to 4 cm, and the depth is in the range of about 0.5-3 cm.

At each end of the tensioner 50 illustrated in FIGS. 6A and 6B, one hole 52, 52', more preferably two holes at each end of the tensioner 50, extend from the top surface 56 through the body of the tensioner 50 to the bottom surface 57 of the tensioner 50. The diameter of each hole 52, 52' is sufficient to easily accommodate the second end 32 of the elongate member 22, 22' of the supplementary stabilization system 10 of the urethral support system 20. In one embodiment, the diameter of each hole 52, 52' is in the range of about 5 mm or less, preferably 3 mm. A plurality of smaller diameter holes 54, 54', for example, linearly arranged at each end of the tensioner 50, extend from the top surface 56, through the body of the tensioner to the bottom surface 57 on both ends of the tensioner 50. The diameter of holes 54, 54' is smaller than holes 52, 52' to allow for pinching or clamping of the second end of the elongate member 22, 22' when the elongate member is pulled from its emergence through the larger holes 52, 52' at the top surface 56 of the tensioner 50 over to the smaller holes 54, 54' thereby pinching, cleating or clamping the second end 32 of the elongate member 22 to the tensioner 50.

As an alternative to the embodiment of the tensioner 50 described above, an adhesive may be used alone or in concert with the holes for attaching the second end 32 of the elongate member 22 to the tensioner 50. In yet another embodiment, the tensioner 50 may include only one hole 52.

Figure 7C:
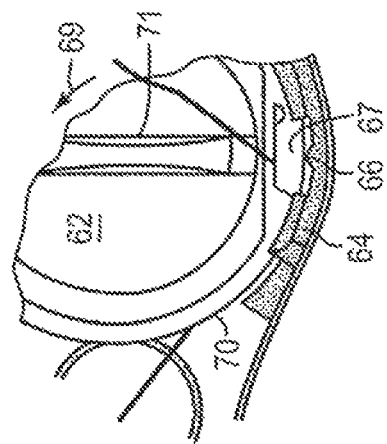
FIGS. 7C-7E illustrate the steps for applying retaining and applying tension to an elongate member by the tensioner illustrated in FIG. 7A.

Referring to FIGS. 7A-7C, in an alternate embodiment, the tensioner comprises a rotary device to provide mechanical advantage by rotary force movement for adjusting the tension on the suburethral support member. The illustrative rotary force tensioner 60 illustrated in an assembled configuration in FIG. 7A and in an exploded format in FIG. 7B, includes a wheel 62 and a wheel ratchet 63. The wheel 62 rotatably locks into the wheel ratchet 63 by, for example, a clip 64, preferably two clips 64, located opposite to one another on the rim 65 of the wheel ratchet 63. At least one ridge 66 perpendicular to the long axis of the wheel ratchet 63 is positioned on the clip 64 and projects towards the center of the wheel ratchet 63.

Figure 7D:
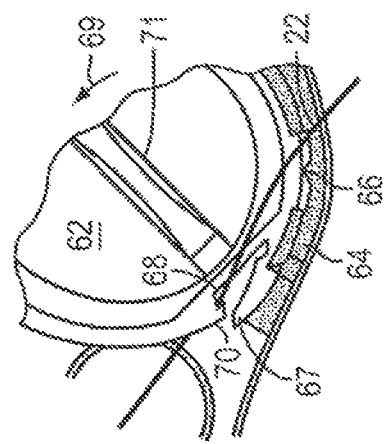
Figure 7E:
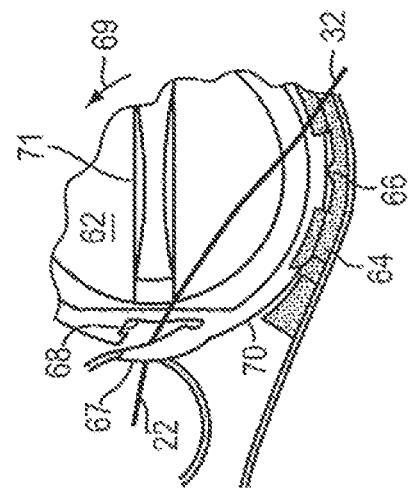

Referring now to FIGS. 7C-E, the wheel 62 includes at least one gate 67 located on the perimeter of the wheel 62. The gate 67 is a partially detached wedge-like portion of the outer rim 70 of the wheel 62. The second end 32 of the elongate member 22 passes between the gate 67 and the inner rim 68 of the wheel 62. As the wheel 62 is manually rotatably ratcheted on the wheel ratchet 63 by rotating the knob 71 indicated by arrow 69 in FIG. 7D, the gate 67 is compressed by the ridge 66 against the inner rim 68 and the elongate member 22 is locked within the tensioner 50 between the gate 67 and the inner rim 68 of the wheel 62 as illustrated in FIG. 7E.

In one aspect, the invention relates to a kit for treatment of urinary incontinence. In one embodiment, the kit includes a urethral support stabilization system. The urethral support stabilization system includes a first and second elongate member, a first and second stabilizer and optionally a urethral support member, for example a mesh sling. In one embodiment, each of the elongate members comprise an absorbable, non-porous material, without interstices that would permit cellular ingrowth. In another embodiment, each of the stabilizers comprise a substantially planar member with multiple radii, i.e., beads as described above projecting from the edge of the planar surface. The stabilizer may further feature a throughhole at one end. In another embodiment, the kit of the invention may further include a tensioner including a hole for pinching the end of an elongate member or an adhesive for adhering to an elongate member.

Figure 8A:
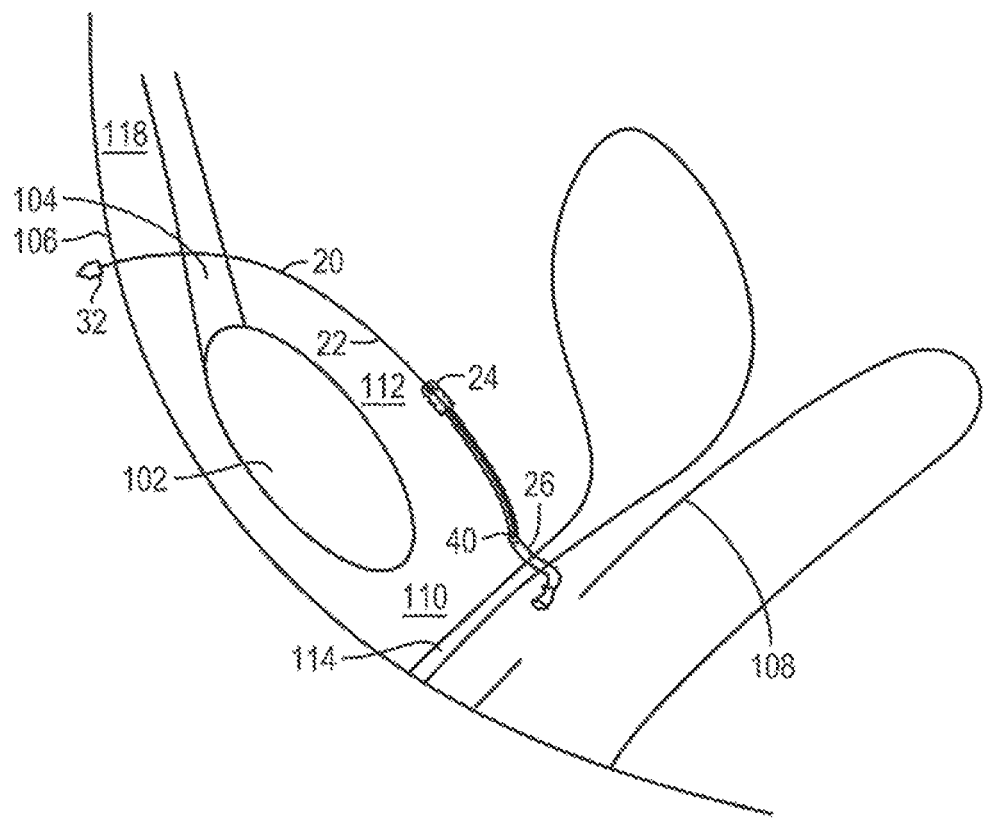
FIG. 8A illustrates a sagittal section and FIGS. 8B and 8C illustrate a transverse section of the pelvic area illustrating the steps in a method for treating the pelvic floor, for example, for treating urinary incontinence according to an embodiment of the invention.
Figure 8B:
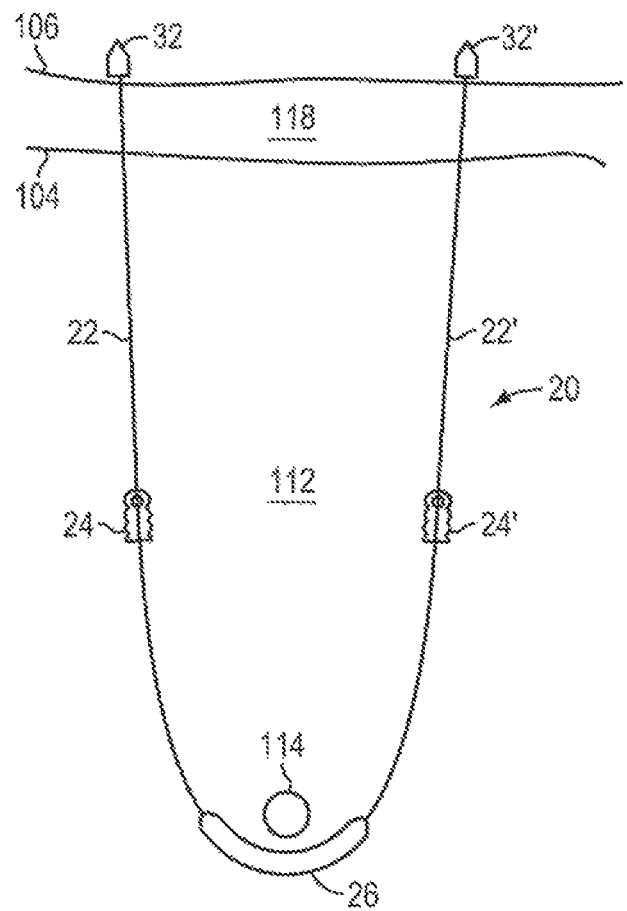
Figure 8C:
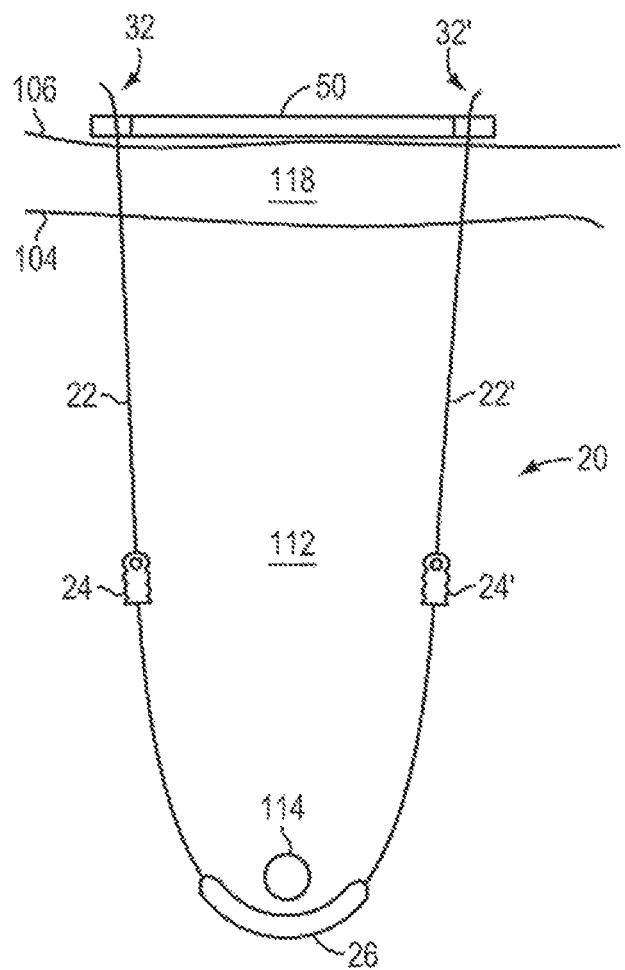

In another aspect, the invention relates to a method for providing urethral support in a patient, such as, for the therapy of female urinary incontinence, and/or uterovaginal prolapse, for example. Referring to FIGS. 8A to 8C, in one embodiment of the method of the invention, a surgeon takes a vaginal to abdominal skin approach by incising the vaginal wall 108 to provide a site for the introduction of the urethral support system 20, described above, to the para-urethral area, i.e., adjacent to the urethra. The supplementary stabilization system 10 including the first elongate member 22 led by the second 32 or free end, is passed through the vaginal incision, around one side of the urethra 114, through the soft tissue of the retro-pubic space 112, behind the pubic bone 102, through the rectus sheath 104, subcutaneous tissue 118, and abdominal skin 106 to emerge on the surface of the abdominal skin 106 at a first abdominal location. According to one embodiment, the first end 30 of the first elongate member 22 of the supplementary stabilization system 10 is pre-attached to the first stabilizer 24. Alternatively, the first end 30 of the first elongate member 22 of the supplementary stabilization system 10 is attached to the first stabilizer 24 during the surgical procedure. In yet another embodiment, the elongate member and stabilizer are detachable.

In one embodiment, the first stabilizer 24 is positioned in the soft tissue of the retropubic space 112, while the elongate member 22 emerges from the abdominal skin 106. The first stabilizer 24 is positioned in the retropubic space, i.e., it does not pass through any of the intervening tissues i.e., rectus sheath, subcutaneous tissue and skin, between the retropubic space and the skin surface.

The first end 40 of the urethral support member 26 is pre-attached to the first stabilizer 24. Alternatively, the first end 40 of the urethral support member 26 is attachable and detachable to the first stabilizer 24 during the surgical procedure. A portion of the urethral support member 26, for example, a first portion extending from approximately the mid-point to one end of the urethral support member, is positioned on the side of the urethra 114 through which the first elongate member 22 passed.

This procedure is repeated with the second elongate member 22', second stabilizer 24', and the support member 26 on the other side of the urethra 114. As with the first stabilizer 24, the second stabilizer 24' is positioned in the retropubic space but at a location different than the first stabilizer 24. The second stabilizer 24' does not pass through any of the intervening tissues i.e., rectus sheath, subcutaneous tissue and skin, between the retropubic space and the skin surface. Following introduction of the second elongate member 22' and the second stabilizer 24', the remaining urethral support member 26 is positioned under the urethra 114 with one end of the support member on one side of the urethra 114 and the other end of the support member on the other side of the urethra 114.

In one embodiment, the first stabilizer 24 and the second stabilizer 24' cannot extend into the intervening tissues between the retropubic space and the skin surface largely because the length of the urethral support member 26 from its midpoint under the urethra to one end of the urethral support member and the length of the suspending member, if one is used, that is positioned on one side of the urethral support member to which the stabilizer is connected, is shorter than the distance between the urethra and the rectus sheath.

Referring to FIG. 8B, following the emergence of the second elongate member 22' at a second abdominal location, the position of the urethral support member 26 under the urethra is adjusted and stabilized by applying tension via the supplementary stabilization system 10 to one, the other, or both of the first 22 elongate member and second elongate member 22'. Tension may be applied manually, i.e., by hand without mechanical aids or by a system that includes mechanical aids such as by mechanically applying rotary or linear force movement, and, further, may measure and or regulate the applied tension. The tension is transmitted from the elongate members to the first and second stabilizers 24, 24'. For example, by applying tension such as by pulling the first elongate member 22 at its second end 32, the first stabilizer 24 advances through the soft tissue while the second stabilizer 24' is withdrawn through the soft tissue along the path already taken by the second stabilizer 24'.

Referring to FIG. 8C, in one embodiment of the method of the invention, the supplementary stabilization system 10 further includes the tensioner 50, such as the tensioner 50 described above with respect to FIGS. 6A and 6B. The exemplary tensioner 50 is joined to the free ends 32, 32' of the first and second elongate members 22, 22', respectively, emerging through, for example, the abdominal skin 106. The tension of the urethral support member 26 is adjusted by applying tension to the second end 32, 32', respectively, of the first and second elongate members 22, 22'. The urethral support member 26 may be moved from side-to-side because the stabilizer 24, 24', illustrated in FIGS. 3A and 3B, may be pulled back and forth in the soft tissues in contrast to prior art devices which have prongs, hooks, barbs or other obtrusive projections to prevent the device from being withdrawn from the soft tissue along the path of entry.

In another embodiment, the surgeon takes a vaginal to perineal approach. The perineum corresponds to the outlet of the pelvis inferior to the pelvic diaphragm (levator ani and coccygeus). The boundaries of the perineum are provided by the pubic arch and the arcuate ligament of the pubis, the tip of the coccyx and on either side of the inferior rami of the pubis and ischium, and the sacrotuberous ligament. A line joining the anterior parts of the ischial tuberosities divides the perineum into two portions, the posterior anal triangle portion and the smaller anterior urogenital triangle.

Figure 9A:
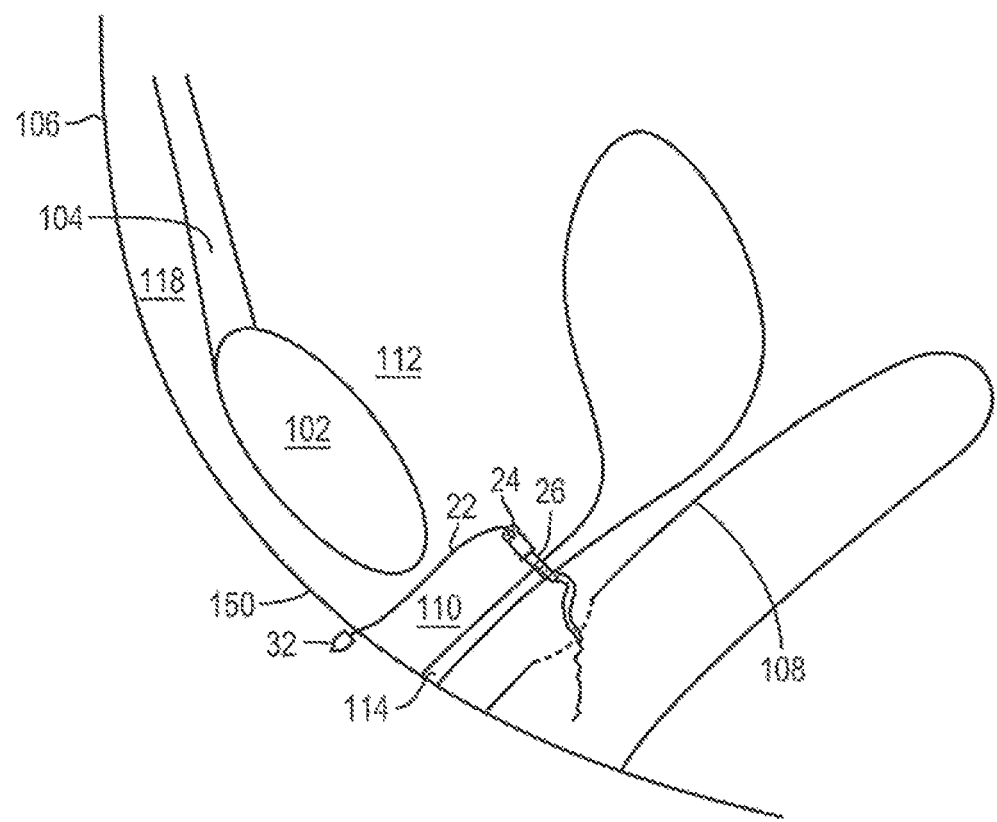
FIG. 9A illustrates a sagittal section taken at 9A-9A in FIG. 9B.
Figure 9B:
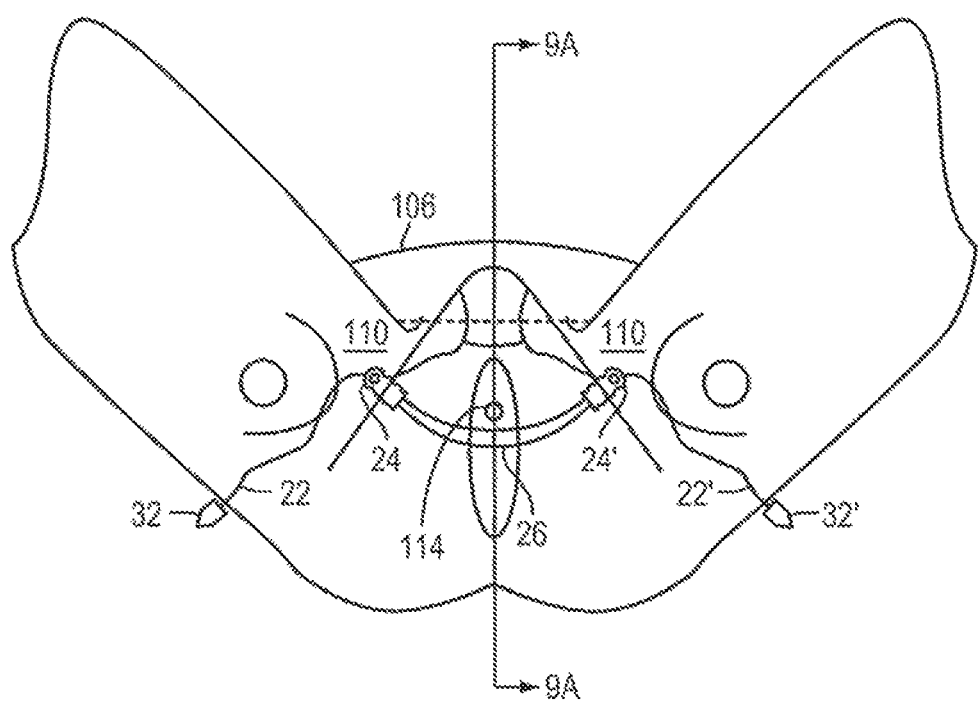
FIG. 9B illustrates a transverse section of the pelvic area illustrating the steps in a method for treating the pelvic floor, for example, for treating urinary incontinence, according to another embodiment of the invention.

In the vaginal to perineal approach, referring now to FIGS. 9A and 9B, a surgeon incises the vaginal wall 108 to provide a site for the introduction of the urethral support system 20, described above, to the para-urethral area. The supplementary stabilization system 10 including the first elongate member 22 led by the second 32 or free end, is passed through the vaginal incision, around one side of the urethra 114, through the soft tissues of the perineal space 110 including the perineal muscles and towards and behind the inferior pubic ramus, but not through the obturator foramen, through the subcutaneous tissue underlying the skin of the perineum 150, emerging on the surface of the perineal skin 150 at a first perineal location.

The first stabilizer 24 is positioned in the soft tissues of the perineal space 110 while the elongate member 22 emerges from the perineal skin 150. The first stabilizer 24 is positioned in the soft tissue of the perineal space 110, i.e., the first stabilizer 24 does not pass through the skin.

The first end 40 of the support member 26 is pre-attached to the first stabilizer 24. Alternatively, the first end 40 of the support member 26 is attachable and detachable to the first stabilizer 24 during the surgical procedure. The support member 26 is positioned on the side of the urethra 114 through which the first elongate member 22 passed.

Referring to FIG. 9B, this procedure is repeated with the second elongate member 22', second stabilizer 24' and the support member 26 on the other side of the urethra 114. As with the first stabilizer 24, the second stabilizer 24' is positioned in the perineal space 110 at a location different than the first stabilizer 24. The second stabilizer 24' does not pass through the skin. Neither the first stabilizer 24 nor the second stabilizer 24' are positioned at a location above the endopelvic fascia. Moreover, the urethral support system used for a vaginal to perineal approach does not extend through the abdominal wall or the obturator foramen. Following introduction of the second elongate member 22' and the second stabilizer 24', the urethral support member 26 is positioned under the urethra 114 with one end of the urethral support member 26 on one side of the urethra 114 and the other end of the urethral support member 26 on the other side of the urethra 114.

In one embodiment, the first stabilizer 24 and the second stabilizer 24' cannot extend into the intervening tissue between the perineal space and the skin surface because the length of the urethral support member from its midpoint on one side of the urethra to one end of then urethral support member and the length of the suspending member, if one is used, is less than the distance between the urethra and the perineal skin. Typically, for the vaginal to perineal approach the length of the urethral support member from its midpoint on one side of the urethra and the suspending member on the same side of the urethra, if one is used, is in the range of about 3 to 6 cm, preferably 4 cm.

Following the emergence of the second elongate member 22' at a second perineal skin location, the position of the urethral support member 26 under the urethra is adjusted and stabilized by applying tension to one or the other of the first 22 and second elongate member 22', or both. Tension may be applied manually, i.e., by hand without mechanical aids or by a system that includes mechanical aids such as by mechanically applying rotary or linear force movement, and further, may measure and or regulate the applied tension. As discussed above, the tension is transmitted from the elongate members to the first and second stabilizers 24, 24'. For example, applying tension such as by pulling the second end 32 of the first elongate member 22, the first stabilizer 24 advances through the soft tissue while the second stabilizer 24' is withdrawn through the soft tissue along the path already taken by the second stabilizer 24'.

A first tensioner 50 is joined to the free end 32 of the first elongate member 22 of the supplementary stabilization system 10 that emerges through the perineal skin at a first location. A second tensioner 50 is joined to the free end 32' of the second elongate member 22' of the supplementary stabilization system 10 emerging through the perineal skin at a second location. The tension of the urethral support member 26 is adjusted by applying tension to the first elongate member 22 and the second elongate member 22'.

In one embodiment, the skin locations may be on the medial aspect of the thighs.

In another embodiment of the method of the invention, the stabilizers 24, 24' are positioned in the pre-pubic soft tissue and the ends 32 of the first and second elongate members 22, 22' emerge through the pre-pubic skin.

Alternatively, the route through tissues can be reversed, for example, for an abdominal to vaginal approach, the urethral support system would pass through tissues in the following order, abdominal skin at a first location, subcutaneous tissue, rectus sheath, retropubic space, suburethral space, and finally, through the vaginal incision. These steps would be repeated on the other side starting at a second abdominal skin location.

For a perineal to vaginal approach, the urethral system would pass through tissues in the following order, perineal skin at a first location, subcutaneous perineal tissue, perineal muscles, suburethral space and finally through a vaginal incision. The steps would be repeated on the other side starting at a second perineal skin location.

Regardless of the surgical approach, according to the invention, intra-operative and post operative adjustment of the urethral support member, for example by adjusting the tension applied to the urethral support member, may be performed for up to one week, preferably 72 hours after surgery. For example, in one embodiment of the method, the tensioner 50 is left in place for 1 to 7 days following implantation of the urethral support member 26. The ends 32 of the first and second elongate members 22, 22' emerging through the abdominal wall, perineal skin, or pre-pubic skin as the case may be, are transected after first applying tension to the free ends 32, 32' to pull a portion of the elongate members 22, 22' adjacent to the free end from below the skin, through the skin, to the skin surface. The portion of the elongate member that was below the skin is cut so that the remnant of the elongate member after cutting that was under tension retracts back under the skin. The same procedure is repeated with the elongate member emerging at the second abdominal, perineal, or pre-pubic location, as the case may be. The one or more tensioners are removed from the patient.

In a particular embodiment of the method of the invention, the vaginal incision is closed, e.g., by suturing followed by adjustment of the tension of the urethral support member by transmitting tension from the elongate members through the stabilizers to the urethral support member.

What is claimed is:

1. A method of post-operatively adjusting a urethral support in treating urinary incontinence of a woman, the method comprising:
    forming an incision in a vagina of the woman;
    passing a support through the incision and locating the support under a urethra, where the support is a porous mesh adapted to allow tissue in-growth; and
    adjusting the support by applying tension to one of a first member and a second member to adjust a position of a stabilizer that is secured between the first member and a first end of the support, the second member being secured to a second end of the support, where each of the first member and the second member has an end that exits skin of the woman, and where each of the first member and the second member is adapted to prevent tissue in-growth into the first member and the second member.

2. The method of claim 1, comprising implanting the support under the urethra, where the support is adapted to allow fibroblast growth through the support.

3. The method of claim 1, comprising applying tension to one of the first member and the second member, where each of the first member and the second member is adapted to slide in two directions including a first direction from the support toward the skin and a second direction from the skin toward the support.

4. The method of claim 1, comprising fine-tuning a position of the stabilizer.

5. The method of claim 1, further comprising measuring tension applied to one of the first member and the second member.

6. The method of claim 1, further comprising regulating tension applied to one of the first member and the second member.

7. The method of claim 1, comprising passing the end of each of the first member and the second member through abdominal skin of the woman.

8. The method of claim 1, comprising passing the end of each of the first member and the second member through perineal skin of the woman.

9. The method of claim 1, comprising passing the end of each of the first member and the second member through skin of a thigh of the woman.

10. The method of claim 1, comprising passing the end of each of the first member and the second member through pre-pubic skin of the woman.

11. The method of claim 1, comprising post-operatively adjusting the support 24 hours after implanting the support.

12. The method of claim 1, comprising post-operatively adjusting the support after a time between 1 day and 7 days after implanting the support.

13. The method of claim 1, further comprising applying tension to the end of the first member, cutting the first member, and allowing a remnant of the first member to retract under the skin.

14. The method of claim 1, further comprising post-operatively adjusting the support by loosening one of the first member and the second member.

15. The method of claim 1, comprising applying tension to one of the first member and the second member, where each of the first member and the second member is coated with a material adapted to ease sliding of the first member and the second member in soft tissue.

16. A method of post-operatively adjusting a urethral support in treating urinary incontinence of a woman, the method comprising:
  forming an incision in a vagina of the woman;
  passing a support through the incision and locating the support under a urethra, where the support is a porous mesh adapted to allow tissue in-growth;
  passing a free end of a first member out of a first skin exit, where the first member includes an opposing second end that is secured to the support via a stabilizer;
  passing a free end of a second member out of a second skin exit, where the second member includes an opposing second end that is secured to the support; and
  adjusting the support by applying tension to one of the first member and the second member to adjust a position of the stabilizer;
  wherein each of the first member and the second member is adapted to prevent tissue in-growth into the first member and the second member.

* * * * *